(12) United States Patent
Gillies et al.

(10) Patent No.: US 11,879,012 B2
(45) Date of Patent: Jan. 23, 2024

(54) METHOD OF MODULATING CELL PROLIFERATION

(71) Applicants: Peter Gillies; METRO NORTH HOSPITAL AND HEALTH SERVICE, Herston (AU)

(72) Inventors: Peter Gillies, Kenmore (AU); Damien G. Harkin, Forest Lake (AU); Neil A. Richardson, Wishart (AU)

(73) Assignees: Peter Gillies, Kenmore (AU); METRO NORTH HOSPITAL AND HEALTH SERVICE, Queensland (AU)

( * ) Notice: Subject to any disclaimer, the term of this patent is extended or adjusted under 35 U.S.C. 154(b) by 292 days.

(21) Appl. No.: 16/976,577

(22) PCT Filed: Mar. 4, 2019

(86) PCT No.: PCT/AU2019/050181
§ 371 (c)(1),
(2) Date: Aug. 28, 2020

(87) PCT Pub. No.: WO2019/165513
PCT Pub. Date: Sep. 6, 2019

(65) Prior Publication Data
US 2020/0407451 A1    Dec. 31, 2020

(30) Foreign Application Priority Data

Mar. 2, 2018   (AU) ............................... 2018900681

(51) Int. Cl.
| | |
|---|---|
| C07K 16/28 | (2006.01) |
| A61K 31/713 | (2006.01) |
| C12N 15/113 | (2010.01) |
| A61K 45/06 | (2006.01) |

(52) U.S. Cl.
CPC ........ *C07K 16/2854* (2013.01); *A61K 31/713* (2013.01); *C12N 15/113* (2013.01); *A61K 45/06* (2013.01)

(58) Field of Classification Search
CPC .......... C07K 16/2854; C07K 14/70564; A61K 31/713; A61K 45/06; C12N 15/113; G01N 2333/70564; G01N 33/57492; G01N 2800/52; A61P 35/00
See application file for complete search history.

(56) References Cited

U.S. PATENT DOCUMENTS

2002/0031508 A1 * 3/2002 Wagner .................. A61P 35/00
                                                              424/94.63
2007/0231332 A1   10/2007 Karbassi et al.

FOREIGN PATENT DOCUMENTS

| EP | 1288222 A1 | 3/2003 |
| WO | 2007117432 A2 | 10/2007 |
| WO | WO-2007117432 A2 * | 10/2007 | ....... G01N 33/57415 |
| WO | 2009140383 A2 | 11/2009 |
| WO | WO-2011094149 A1 * | 8/2011 | ........... A61K 31/726 |
| WO | WO-2015161192 A1 * | 10/2015 | ........... A61K 31/337 |

OTHER PUBLICATIONS

Shamay Y et al. P-selectin is a nanotherapeutic delivery target in the tumor microenvironment. Sci Transl Med 2016 8(345): 345ra87 (Year: 2016).*
Yang Y et al. Plant food delphinidin-3-glucoside significantly inhibits platelet activation and thrombosis: novel protective roles against cardiovascular diseases. PLoS One 2012;7(5):e37323 (Year: 2012).*
Zou J et al. Curcumin increases breast cancer cell sensitivity to cisplatin by decreasing FEN1 expression. Oncotarget. 2018; 9:11268-11278 (Year: 2018).*
Verena MC et al. Discrepancies between metabolic activity and DNA content as tool to assess cell proliferation in cancer research. J Cell Mol Med. 2010 14(4):1003-13 (Year: 2010).*
Lin HJ et al. Curcumin blocks migration and invasion of mouse-rat hybrid retina ganglion cells (N18) through the inhibition of MMP-2, -9, FAK, Rho A and Rock-1 gene expression. Oncology reports 2010 23:665-670 (Year: 2010).*
Riss T Is Your MTT Assay Really the Best Choice? Promega Resource 2016 Web Archive https://web.archive.org/web/20160830234016/http://www.promega.com:80/resources/pubhub/is-your-mtt-assay-really-the-best-choice (Year: 2016).*
Matsumoto H et al. Orally Administered Delphinidin 3-Rutinoside and Cyanidin 3-Rutinoside Are Directly Absorbed in Rats and Humans and Appear in the Blood as the Intact Forms. J. Agric. Food Chem. 2001; 49, 1546-1551) (Year: 2001).*
Feller LL et al. Oral squamous cell carcinoma in relation to field precancerisation: pathobiology. Cancer Cell International 2013 13, Article No. 31. (Year: 2013).*
Wang ZM et al. ROCK inhibitor Y-27632 inhibits the growth, migration, and invasion of Tca8113 and CAL-27 cells in tongue squamous cell carcinoma. Tumor Biol. (2016) 37:3757-3764 (Year: 2016).*
Shi J et al. Activation of ERK-FAK Signaling Pathway and Enhancement of Cell Migration Involved in the Early Interaction Between Oral Keratinocytes and Candida albicans. Mycopathologia (2009) 167:1-7 (Year: 2009).*
Guo SW, et al., 'P-selectin as a potential therapeutic target for endometriosis,' Fertility and Sterility, (2015), vol. 103 No. 4, pp. 990-1000.
Sadok A, et al., 'Rho Kinase Inhibitors Block Melanoma Cell Migration and Inhibit Metastasis,' Cancer Research, (2015), vol. 75 issue 11, pp. 2272-2284.
International Preliminary Report on Patentability and Written Opinion received from the The International Bureau of WIPO in connection to International Application No. PCT/AU2019/050181 dated Sep. 8, 2020.

(Continued)

*Primary Examiner* — Julie Wu
*Assistant Examiner* — John J Skoko, III
(74) *Attorney, Agent, or Firm* — Carter, DeLuca & Farrell LLP; George Likourezos; Carmella L. Stephens

(57) ABSTRACT

This invention relates generally to a method of inhibiting epithelial cell proliferation including the treatment of conditions associated with aberrant epithelial cell proliferation in mammals, including animals and humans. The present invention is particularly relevant for the treatment of cancer.

8 Claims, 9 Drawing Sheets

Specification includes a Sequence Listing.

(56) References Cited

OTHER PUBLICATIONS

Chen JL, et al. 'Inhibition of P-selectin L-EGF monoclonal antibody on metastasis of human gastric carcinoma in severe combined immunodeficient mice,' World Chinese Journal of Digestology, (2005), vol. 13, No. 23, pp. 279 I-2794. (Abstract Only).

Wei Lei, et al. "Novel Insights Into the Roles of Rho Kinase in Cancer", Archivum Immunologiae ET Therapiae Experimentalis, Birkhaeuser Verlag AG, CH, vol. 64, No. 4, pp. 259-278; Jan. 2, 2016.

Hostettler Nina, et al.,"P-selection-and heparanase-dependent antimetastatic activity of non-anticoagulant heparins", The FASEB Journal, vol. 21, No. 13, pp. 3562-3572; Jun. 8, 2007.

Shamay Yosi, et al. "P-selection is a nanotherapeutic delivery target in the tumor microenvironment", Science Translational Medicine, vol. 8, No. 345, pp. 1-28, Jun. 29, 2016.

Chen, Jin-Lian, et al., "Effect of P-selectin monoclonal antibody on metastasis of gastric cancer and immune function", Introduction China World Journal of Gastroenterology, vol. 9, No. 7, pp. 1607-1610, Jan. 1, 2003.

Euroepan Extended Search Report issued by the European Patent Office in connection with International Application No. 19760826.8, dated Nov. 15, 2021.

\* cited by examiner

SEQUENCE LISTING

```
<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: Synthetic

<400> SEQUENCE: 1
catgtacgtt gctatccagg c                                              21

<210> SEQ ID NO 2
<211> LENGTH: 21
<212> TYPE: DNA
<213> ORGANISM: Artificial Sequence
<220> FEATURE:
<223> OTHER INFORMATION: Synthetic

<400> SEQUENCE: 2
ctccttaatg tcacgcacga t                                              21

<210> SEQ ID NO 3
<211> LENGTH: 23
<212> TYPE: DNA
<213> ORGANISM: Artificial Sequence
<220> FEATURE:
<223> OTHER INFORMATION: Synthetic

<400> SEQUENCE: 3
ctgttaccct ggattctatg ggc                                            23

<210> SEQ ID NO 4
<211> LENGTH: 22
<212> TYPE: DNA
<213> ORGANISM: Artificial Sequence
<220> FEATURE:
<223> OTHER INFORMATION: Synthetic

<400> SEQUENCE: 4
gctgcactgc gagttaaaag ag                                             22
```

METHOD OF MODULATING CELL PROLIFERATION

REFERENCE TO SEQUENCE LISTING SUBMITTED VIA EFS-WEB

This application includes an electronically submitted sequence listing in ST.25 format. The ST.25 file contains a sequence listing entitled "35547126 ST25(35547126).txt" which was created on Oct. 23, 2023 and is 1 Kb in size. The sequence listing contained in this ST.25 file is pan of the specification and is hereby incorporated by reference herein in its entirety.

FIELD OF THE INVENTION

This invention relates generally to a method of inhibiting epithelial cell proliferation including the treatment of conditions associated with aberrant epithelial cell proliferation in mammals, including animals and humans. The present invention is particularly relevant for the treatment of cancer.

BACKGROUND OF THE INVENTION

Despite advances in our understanding and therapeutic treatment of many forms of cancer, it remains one of the leading causes of death around the world, with the prevalence of many cancers increasing. Carcinomas represent the most common form of cancer in adults, including nearly all breast, prostate, lung, pancreas, ovarian and colon cancers. Carcinomas develop in the epithelial tissue of the skin, or in the tissue that lines the internal organs, such as the liver or kidneys. These tumours can be benign or malignant, with malignant tumours demonstrating a tendency to invade and infiltrate local and adjacent structures and eventually metastasize to distant sites in the body.

Carcinomas are typically distinguished histologically into a number of different subtypes, including adenocarcinoma, basal cell carcinoma, squamous cell carcinoma, renal cell carcinoma, ductal carcinoma in situ, invasive ductal carcinoma, adenosquamous carcinoma, anaplastic carcinoma, large cell carcinoma, small cell carcinoma and carcinoma of unknown primary. Depending on the type, location and extent of the disease, treatment for carcinoma can include surgery, radiation therapy and chemotherapy. Increasingly, these traditional forms of cancer treatment are supplemented or substituted with targeted therapeutics.

Targeted therapeutics interfere with biological events that drive tumorigenesis. Unlike traditional chemotherapeutics, which exert their effect on rapidly proliferating cells, targeted therapeutics are designed to target the molecular characteristics that distinguish malignant cell populations from normal cells. Accordingly, in order to develop effective targeted therapeutics, it is necessary to identify molecular characteristics that are unique to tumour cells. One approach to identify potential targets is to compare the expression of genes or proteins in cancer cells with those in normal cells. For example, human epidermal growth factor receptor 2 protein (HER-2) is expressed at high levels on the surface of some cancer cells. This differentially expressed target has been exploited using trastuzumab (Herceptin®), which is approved to treat breast and stomach cancers that overexpress HER-2. Another approach is to identify cancer cells that produce mutant forms of proteins that drive cancer progression. For example, the cell signalling protein BRAF is commonly mutated in melanoma. Vemurafenib (Zelborad®) targets the V600E mutant form of BRAF and is approved for the treatment of patients with metastatic melanoma that expresses the mutant BRAF protein.

Although targeted therapeutics have proven to be successful in the treatment of a broad range of tumour types, many tumours develop resistance to targeted therapeutics by acquiring additional mutations that render the targeted therapeutic ineffective, or by upregulating alternative pathways to reduce or eliminate dependence on the target. Therefore, combination approaches are widely recognized to be more effective in obtaining long-term results in the treatment of many tumour types. For example, it has recently been demonstrated that the use of two therapies that target different parts of the signalling pathway that is altered by the BRAF V600E mutation in melanoma is more effective in slowing disease progression and the development of resistance compared to the use of single agents (Flaherty et al. 2012, *New England Journal of Medicine*, 367(18): 1694-1703). Whilst such treatments have shown some clinical promise, their therapeutic efficacy is largely restricted to specific proliferative disorders.

Accordingly, there is still an ongoing need for more effective therapeutic options for the treatment of conditions associated with aberrant cell proliferation, in particular, cancer.

SUMMARY OF THE INVENTION

This disclosure is predicated, at least in part, on the surprising finding that inhibiting P-selectin expression and/or activity in epithelial cells is inhibitory to epithelial cell proliferation. This finding has been reduced to practice in a method for inhibiting epithelial cell proliferation in mammals, including animals and humans.

Accordingly, in one aspect, there is provided a method of inhibiting epithelial cell proliferation, the method comprising exposing an epithelial cell to an agent that inhibits P-selectin expression and/or activity.

In a second aspect, there is provided a method for treating a condition associated with aberrant epithelial cell proliferation, the method comprising administering to a subject an effective amount of an agent that inhibits P-selectin expression and/or activity.

In a third aspect, there is provided a use of an agent that inhibits P-selectin expression and/or activity in the manufacture of a medicament for the treatment of a condition associated with aberrant epithelial cell proliferation.

In a fourth aspect, there is provided a method for treating a condition associated with aberrant epithelial cell proliferation, the method comprising:
a. obtaining a sample of epithelial cells from a subject;
b. determining the level of P-selectin expression in the sample;
c. comparing the level of P-selectin expression to a reference value, wherein a level of P-selectin in comparison to the reference value is indicative of the presence of a condition associated with aberrant cell proliferation; and
d. treating a subject identified in step (c) as having a condition associated with aberrant epithelial cell proliferation with an agent that inhibits P-selectin expression and/or activity.

In a fifth aspect, there is provided a pharmaceutical composition comprising an agent for inhibiting P-selectin expression and/or activity for use in the treatment of a condition associated with aberrant epithelial cell proliferation.

BRIEF DESCRIPTION OF THE DRAWINGS

Embodiments of the disclosure are described herein, by way of non-limiting example only, with reference to the accompanying drawings.

DETAILED DESCRIPTION OF THE INVENTION

Figure 1:
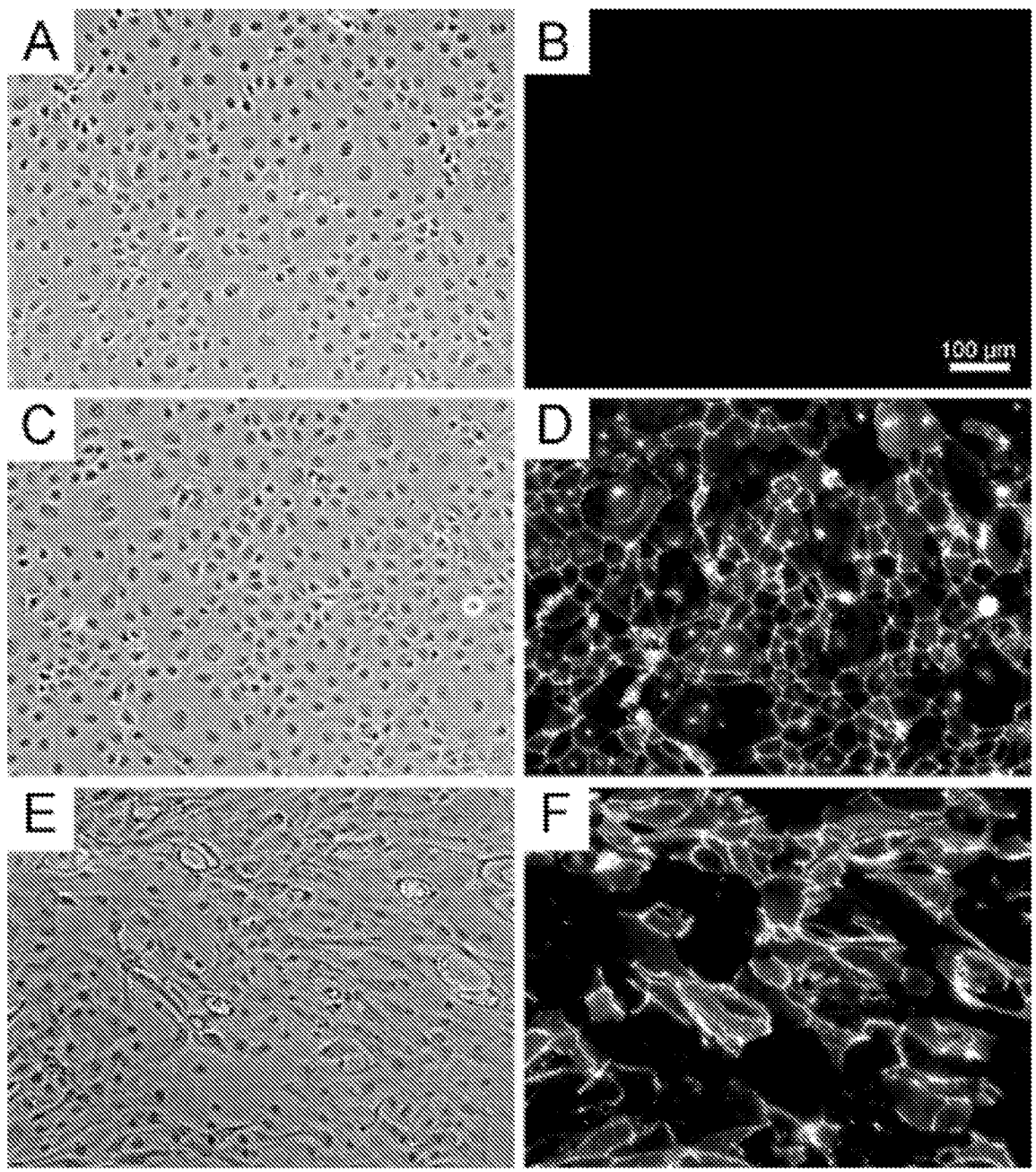
FIG. 1 is a photographic representation of cultured human corneal epithelial cells expressing P-selectin. Initial screening of the SV-40 transformed cell line HCE-T (A-D) show positive staining for P-selectin (D) compared to control cells (B). A similar pattern of staining at cell-cell boundaries was also observed in first passage (p1) cultures derived from freshly isolated corneal-limbal epithelial cells (p0). Scale bar is representative of 100 μm.

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. All patents, patent applications, published applications and publications, databases, websites and other published materials referred to throughout the entire disclosure, unless noted otherwise, are incorporated by reference in their entirety. In the event that there is a plurality of definitions for terms, those in this section prevail. Where reference is made to a URL or other such identifier or address, it understood that such identifiers can change and particular information on the internet can come and go, but equivalent information can be found by searching the interne. Reference to the identifier evidences the availability and public dissemination of such information.

The articles "a", "an" and "the" include plural aspects unless the context clearly dictates otherwise. Thus, for example, reference to "an agent" includes a single agent, as well as two or more agents; reference to "a treatment" includes a single treatment, as well as two or more treatments; and so forth.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

As used herein, the term "agent" includes a compound that induces a desired pharmacological and/or physiological effect. The term also encompasses pharmaceutically acceptable salts, esters, amides, prodrugs, active metabolites, analogs and the like. When the above term is used, it will be understood by persons skilled in the art that this includes the active agent per se as well as pharmaceutically acceptable, pharmacologically active salts, esters, amides, prodrugs, metabolites, analogs, etc. The term "agent" is not to be construed narrowly but also extends to small molecules, proteinaceous molecules such as peptides, polypeptides and proteins, as well as compositions comprising them and nucleic acid molecules such as RNA, DNA and mimetics and chemical analogs thereof as well as cellular agents. The term "agent" also includes a cell which is capable of producing and secreting the agents referred to herein, as well as polynucleotides comprising a nucleic acid sequence that encodes one or more such agents. Thus, the term "agent" extends to nucleic acid constructs including vectors, such as viral or non-viral vectors, expression vectors and plasmids for expression in and secretion in a range of cells.

The term "subject" as used herein refers to mammals and includes humans, primates, livestock animals (e.g. sheep, pigs, cattle, horses, donkeys), laboratory test animals (e.g. mice, rabbits, rats, guinea pigs), companion animals (e.g. dogs, cats) and captive wild animals (e.g. foxes, kangaroos, deer). Typically, the mammal is human, laboratory test animal or companion animal. More typically, the mammal is a human.

As used herein, the term "effective amount" includes a non-toxic but sufficient amount of an agent which is effective for inhibiting P-selectin expression and/or activity. The effective amount required will vary from subject to subject depending on one or more relevant factors, illustrative examples of which include the species of the subject to be treated, the age and general health and wellbeing of the subject and the mode of administration. Thus, it may not be possible to specify an exact "effective amount". However, for any given case, an appropriate "effective amount" may be determined by one of ordinary skill in the art using only routine experimentation.

As used herein, the terms "treating", "treatment", and the like refer to any and all methods which remedy, prevent, hinder, retard, ameliorate, reduce, delay or reverse the progression of a condition associated with aberrant epithelial proliferation, including one or more undesirable symptoms thereof. Thus, the terms "treating", "treatment" and the like are to be considered in their broadest context. For example, treatment does not necessarily imply that a patient is treated until total recovery. Conditions associated with aberrant epithelial cell proliferation are typically characterized by multiple symptoms, and thus the treatment need not necessarily remedy, prevent, hinder, retard, ameliorate, reduce, delay or reverse all of said symptoms. Methods disclosed herein may involve "treating" a condition associated with aberrant epithelial cell proliferation in terms of reducing or ameliorating the occurrence of a highly undesirable event or symptom associated with the condition or an outcome of the progression of the condition, but may not of itself prevent the initial occurrence of the event, symptom or outcome. Accordingly, treatment includes amelioration of the symptoms of the condition associated with aberrant epithelial cell proliferation or preventing or otherwise reducing the risk of developing symptoms of the condition.

As used herein, the terms "prevent", "prevented", or "preventing", as used herein, refer to a prophylactic regime that reduces the incidence of conditions associated with aberrant epithelial cell proliferation in a subject or decreases the likelihood that the subject will develop a condition associated with aberrant epithelial cell proliferation.

In the context of the present disclosure, the terms "inhibiting" and variations thereof such as "inhibition" and "inhibits" do not necessarily imply the complete inhibition of the specified event, activity or function. Rather, the inhibition may be to an extent, and/or for a time, sufficient to produce the desired effect. Inhibition may be prevention, retardation, reduction or otherwise hindrance of the event, activity or function. Such inhibition may be in magnitude and/or be temporal in nature. In particular contexts, the terms "inhibit" and "prevent", and variations thereof may be used interchangeably.

Inhibiting Epithelial Cell Proliferation

The present disclosure describes the inhibition of epithelial cell proliferation, which is predicated on the unexpected finding that inhibition of P-selectin expression and/or activity is sufficient to inhibit epithelial cell proliferation. Accordingly, provided herein are methods for inhibiting epithelial cell proliferation by exposing an epithelial cell to an agent that inhibits P-selectin expression and/or activity.

P-selectin, also known as CD62P, Granule Membrane Protein 140 (GMP-140) and Platelet Activation-Dependent Granule to External Membrane Protein (PADGEM), is a 140 kDa cell adhesion molecule comprising nine consensus repeats that is normally expressed in α-granules of activated platelets and Weibel-Palade bodies (WPB) of endothelial cells. The primary ligand for P-selectin is PSGL-1 (P-selectin glycoprotein ligand-1), which is constitutively found on all leukocytes. Other ligands for P-selectin include CD24, CD44 and polysulfated ligands such as glycosaminoglycans (e.g., chondroitin sulfate and heparan sulfate). Previous studies have suggested that the normal tissue distribution of P-selectin is only on the surface of activated platelets and vascular endothelial cells (McEver et al., (1989) *Journal of Clinical Investigation*, 84: 92-99). Others have also shown that P-selectin is expressed in the breast cancer endothelium (Fox et al., (1995), *Journal of Pathology*, 177: 369-376; Fox et al., (1995) *Breast Cancer Research and Treatment*, 36: 219-226) and some epithelial tumour cell lines (Iwamura et al., (1997) *Cancer Research*, 57: 1206-1212).

The term "epithelial cell" as used herein refers to a cell or cells that form part of the epithelium of organs, as well as those that make up glands and the outer surface of the body. Epithelial cells can comprise squamous epithelial cells, columnar epithelial cells, adenomatous epithelial cells or transitional epithelial cells. Epithelial cells can be arranged in single layers or multiple layers, depending on the organ and location. Types of epithelial cells will be familiar to persons skilled in the art, illustrative examples of which include keratinocyte epithelial cells and non-keratinocyte epithelial cells.

Keratinocytes form the squamous epithelium that is found at anatomic sites such as the skin, ocular surface, oral mucosa, esophagus and cervix. Examples of keratinocyte epithelial cells include dermal keratinocyte, ocular epithelial cells, corneal epithelial cells, oral mucosal epithelial cells, esophagus epithelial cells and cervix epithelial cells. Non-keratinocyte epithelial cells form the epithelium of sites such as breast, prostate, liver, respiratory tract, retina and gastrointestinal tract. Examples of non-keratinocyte epithelial cells include prostate cells, mammary cells, hepatocytes, liver epithelial cells, biliary epithelial cells, gall bladder cells, pancreatic islet cells, pancreatic beta cells, pancreatic ductal epithelial cells, pulmonary epithelial cells, airway epithelial cells, nasal epithelial cells, kidney cells, bladder cells, urethral epithelial cells, stomach epithelial cells, large intestinal epithelial cells, small intestinal epithelial cells, testicular epithelial cells, ovarian epithelial cells, fallopian tube epithelial cells, thyroid cells, parathyroid cells, adrenal cells, thymus cells, pituitary cells, glandular cells, amniotic epithelial cells, retinal pigmented epithelial cells, sweat gland epithelial cells, sebaceous epithelial cells and hair follicle cells.

It is to be understood that, in the context of the present disclosure, epithelial cells will have certain phenotypic, genotypic and/or functional characteristics that distinguish them from other cells types, such as endothelial cells. In an embodiment, an epithelial cell is characterised by the expression of at least one antigen selected from the group consisting of epithelial membrane antigen (EMA or MUC1), cytokeratin, E-cadherin, and epithelium specific antigen (EpCAM). In an embodiment, an endothelial cell is characterised by the expression of at least one antigen selected from the group consisting of CD31, CD34, CD45, ICAM-1/CD54, LYVE-1, Tie-2/Tek, VCAM-1/CD106, VEGF-R2 and von Willebrand factor (vWF).

In an exemplary embodiment, the epithelial cell contemplated by the present disclosure is a cancer cell. The term "cancer cell" as used herein refers to an epithelial cell or cells that have unchecked cell growth. The skilled person would appreciate that the transformation of a normal epithelial cell to a cancer cell results from the acquisition of genetic mutations that can accelerate cell division rates or inhibit normal controls on cell growth, such as cell cycle arrest or programmed cell death. The prolonged growth and division of a cancer cell can develop into a tumour.

It is also to be understood that, in the context of the present disclosure, epithelial cells that have undergone transformation to a malignant state will have certain phenotypic, genotypic and/or functional characteristics that distinguish them from other cell types, such as normal or malignant endothelial cells. In an embodiment, a malignant epithelial cell is characterised by the expression of antigens selected from the group comprising survivin, cytokeratin, EpCAM, EMA and CA125.

In particular embodiments of the present disclosure, the agent inhibits P-selectin expression. The term "expression" refers to either production of RNA message (gene expression) or translation of RNA message into proteins or polypeptides (protein expression). For example, the term "P-selectin expression" includes (i) the production of P-selectin RNA message (i.e., P-selectin gene expression), (ii) the translation of P-selectin RNA message into P-selectin protein and/or (iii) the transport of P-selectin protein to the cell surface.

The term "gene" as used herein refers to any and all discrete coding regions of the cell's genome, as well as associated non-coding and regulatory regions. The term is intended to mean the open reading frame encoding specific polypeptides, introns, and adjacent 5' and 3' non-coding nucleotide sequences involved in the regulation of expression. In this regard, the gene may further comprise control signals such as promoters, enhancers, termination and/or polyadenylation signals that are naturally associated with a given gene, or heterologous control signals. The DNA sequences may be cDNA or genomic DNA or a fragment thereof. In an exemplary embodiment, the P-selectin contemplated in the methods disclosed herein is human P-selectin encoded by the SELP gene (NCBI Gene ID: 6403).

The terms "polypeptide", "proteinaceous molecule", "peptide" and "protein" are used interchangeably herein to refer to a polymer of amino acid residues and to variants and synthetic analogues of the same. Thus, these terms apply to amino acid polymers in which one or more amino acid residues is a synthetic non-naturally-occurring amino acid, such as a chemical analogue of a corresponding naturally-occurring amino acid, as well as to naturally-occurring amino acid polymers. These terms also include modifications thereto, for example, glycosylations, acetylations, phosphorylations and the like. Soluble forms of the subject proteinaceous molecules are also encompassed herein. Included within the definition are, for example, polypeptides containing one or more analogs of an amino acid including, for example, unnatural amino acids or polypeptides with substituted linkages.

In an exemplary embodiment, the agent inhibits P-selectin gene expression. The skilled person will appreciate that inhibition of P-selectin gene expression may be achieved using a variety of agents that are known in the art. Illustrative agents include but are not limited to, oligodbonucleotide sequences (e.g., anti-sense RNA and DNA molecules), ribozymes, and CRISPR RNAs used in combination with the Cas or other nucleases that function to inhibit the translation of P-selectin transcripts.

Anti-sense RNA and DNA molecules act to directly block the translation of mRNA of P-selection by binding to targeted mRNA and preventing protein translation. In regard to antisense DNA, oligodeoxyribonucleotides derived from the translation initiation site, e.g., between − and + regions are preferred. In some embodiments, anti-sense RNA and DNA molecules are used to directly block the translation of P-selectin mRNA by binding to targeted mRNA and preventing protein translation. In regard to antisense DNA, oligodeoxyribonucleotides derived from the translation initiation site, e.g., between −10 and +10 regions are desirable.

Both anti-sense RNA and DNA molecules and ribozymes may be prepared by any method known to persons skilled in the art for the synthesis of RNA molecules. These include techniques for chemically synthesizing oligodeoxy-ribonucleotides well known in the art such as for example solid phase phosphoramidite chemical synthesis. Alternatively, RNA molecules may be generated by in vitro and in vivo transcription of DNA sequences encoding the antisense RNA, molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various modifications to the DNA molecules may be introduced as a means of increasing intracellular stability and half-life. Possible modifications include but are not limited to the addition of flanking sequences of ribo- or deoxy-nucleotides to the 5' or 3' ends of the molecule or the use of phosphorothioate or 2' O-methyl rather than phosphodiesterase linkages within the oligodeoxyribonucleotide backbone.

RNA interference (RNAi) describes a mechanism of gene silencing that is based on degrading or otherwise preventing the translation of mRNA in a sequence specific manner that is dependent on small, non-coding RNA ~20 to 30-nucleotide (nt) in length. Three classes of small RNA can regulate genes by targeting transcripts in the cytoplasm: microRNAs (miRNAs), which are hairpin-derived RNAs with imperfect complementarity to targets and that cause translational repression; small interfering RNAs (siRNAs), which have perfect complementarity to targets and cause transcript degradation; and PIWI-interacting RNAs (piRNAs), which target transposon transcripts in animal germ lines. All three classes of small RNA share a common mode of action, the minimal effector is a ribonucleoprotein complex comprising an Argonaute family protein bound to a single-stranded ~20 to 30 nt RNA that exhibits specificity by base-pairing interactions with the gene target. In miRNA and siRNA pathways, this is known as the RNA-induced silencing complex (RISC) and it drives the silencing of a target mRNA by degradation and/or transcriptional repression.

In exemplary embodiments, the agent that inhibits P-selectin gene expression is a small interfering RNA (siRNA). It will be appreciated that the skilled person can determine the most suitable siRNA for use in accordance with the disclosed methods by routine experimentation. For example, although it is preferable that the siRNA exhibits 100% complementarity to its target nucleic acid molecule, the siRNA may nevertheless exhibit some degree of mismatch to the extent that hybridization sufficient to induce an RNAi response in a sequence specific manner can be effected. Accordingly, it is preferred that the siRNA of the present disclosure comprises at least 70%-100% sequence complementarity. In an embodiment, the siRNA for use in accordance with the disclosed methods is Mission® esiRNA. Human selp (Sigma-Aldrich Cat. No. EHU039631-5050UG).

In exemplary embodiments, the methods described herein contemplate the use of an agent that inhibits P-selectin activity. The term "activity" as used herein refers to any biological or therapeutic/prophylactic activity. The skilled person would appreciate that inhibition of P-selectin activity may be assessed using a number of experimental techniques that are known in the art. Suitable techniques for assessing the inhibition of P-selectin activity include cell adhesion, ligand binding and competition assays.

In an exemplary embodiment, the agent that inhibits P-selectin activity is an antagonist of P-selectin activity.

The term "antagonist" refers to an agent that interferes with the physiological action of P-selectin. For example, an antagonist may inhibit the binding of P-selectin to a ligand. Alternatively, the antagonist may bind P-selectin and act as a mimetic of key ligands, such as PSGL-1. The skilled person would appreciate that such antagonists are not intended to be limited to a particular material or form. Illustrative examples of suitable antagonists include an anti-P-selectin antibody or an antigen-binding fragment thereof, polymerized liposome nanoparticles (PLNP) that display multiple synthetic, low molecular weight ligands (e.g., John et al., (2003), *FASEB Journal*, 17(15): 2296-2298; Bruehl et al., (2001) *Biochemistry*, 40: 5964-5974), ligand mimetics for P-selectin (e.g., Pochechueva et al., (2002), *Chemical Biology*, 9: 757-762; Kaila & Thomas, (2002), *Medical Research Reviews*, 22: 566-601), P-selectin blockers (e.g., Nishida et al., (2000), *Biomacromolecules*, 1: 68-74), low molecular weight, non-carbohydrate compounds (e.g., Ohta et al., (2001), *Inflammation Research*, 50: 544-551), small molecule inhibitors (e.g., Slee et al., (2001). *Journal of Medicinal Chemistry*, 44: 2094-2107; Kaila et al., (2001), *Bioorganic Medicinal Chemistry*, 9: 801-806; Schon et al., (2002), *Nature Medicine*, 8: 366-372)

In an exemplary embodiment, the antagonist is an anti-P-selectin antibody or an antigen-binding fragment thereof. Others have previously shown that the functional activity of P-selectin can be inhibited through use of an anti-P-selectin antibody or an antigen-binding fragment thereof, an illustrative example of which is described by Owens et al. in U.S. Pat. No. 6,407,214 or by Sanz et al. (2007, *British Journal of Pharmacology*, 152(4): 481-492), incorporated herein by reference. A range of antibodies to P-selectin may be available commercially or they can be synthesised by methods known to those skilled in the art.

The term "antibody" as used herein broadly refers to any immunoglobulin (Ig) molecule comprised of four polypeptide chains, two heavy (H) chains and two light (L) chains, or any functional fragment, mutant, variant, or derivation thereof, which retains the essential epitope features of an Ig molecule. Such mutant, valiant, or derivative antibody formats are known in the art.

In a full size antibody, each heavy chain comprises a heavy chain variable region (HCVR or VH) and a heavy chain constant region. The heavy chain constant region is comprised of three domains, CH1, CH2 and CH3. Each light chain comprises a light chain variable region (LCVR or VL) and a light chain constant region, CL. The VH and VL regions can be further subdivided into regions of hypervariablity, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3 and FR4, Immunoglobulin molecules can be of any type (e.g., IgG, IgE, IgM, IgD, IgA and IgY), class (e.g., IgG1, IgG2, IgG3, IgG4, IgA1 and IgA2) or subclass.

The term "antibody fragment" as used herein means one or more fragments of an antibody that retain the ability to specifically bind to an antigen. Examples of antibody fragments include (i) a Fab fragment, a monovalent fragment consisting of the VL, VH, CL and CH1 domains; (ii) a F(ab')$_2$ fragment, a F(ab')$_2$ fragment, a bivalent fragment comprising two Fab fragments linked by a disulphide bridge at the hinge region; (iii) a Fd fragment consisting of the VH and CH1 domains; (iv) a single-chain variable fragment (scEv) consisting of the VL and VH domains of a single arm of an antibody; (v) a dAb fragment (Ward et al. 1989, *Nature*, 341: 544-6), which comprises a single variable domain; and (vi) an isolated CDR.

The skilled person would appreciate that the inhibition of P-selectin activity is dependent, at least in part, on the expression of P-selectin protein on the surface of the epithelial cell, Methods for determining expression of P-selectin on the cell surface are known in the art. For example, immunohistochemistry and/or fluorescence-activated cell sorting (FACS) can be employed using an anti-P-selectin antibody (or a P-selectin-binding fragment thereof) comprising a detectable label (such as a fluorochrome) to detect the presence of P-selectin protein on the surface of a cell.

Treatment of Conditions Associated with Aberrant Epithelial Cell Proliferation

Embodiments of the present disclosure provide methods for treating a condition associated with aberrant epithelial cell proliferation, the method comprising administering to a subject an effective amount of an agent that inhibits P-selectin expression and/or activity.

The term "condition associated with aberrant epithelial cell proliferation" typically means a condition associated with unwanted or uncontrolled proliferation of excessive normal or abnormal epithelial cells, such as, neoplastic or hyperplastic growth, whether in vitro or in vivo. Conditions associated with aberrant epithelial cell proliferation will be familiar to persons skilled in the art, illustrative examples of which include cancer (e.g., a primary cancer or a metastatic cancer), benign prostatic hyperplasia and prostatitis; colitis and colon polyps; cystic disorders of the breast, ovaries, kidney and liver; bronchitis, sinusitis, pharyngitis and other acute or chronic infections of the upper respiratory system; primary binary cirrhosis; endometriosis and endometritis; vaginitis and vaginosis; cervicitis and cervical infections; bladder infections; bladder wall hyperplasia and other bladder disturbances; dermatitis; eczema; psoriasis and other hyperproliferative skin conditions; benign tumours and autosomal dominant polycystic kidney disease. In an exemplary embodiment, the condition is a cancer.

The development of targeted therapeutics is often concomitant to the identification or stratification of particular patient cohorts that will respond to the targeted therapy. One skilled in the art would recognise that such patient stratification will result in either the identification of a subject who is likely to respond to the targeted therapeutic and conversely, identification of a subject who is unlikely to respond to the targeted therapeutic. In the context of the present disclosure, the skilled person would appreciate that the expression of P-selectin is necessary for treating a subject in accordance with the disclosed methods. Accordingly, in exemplary embodiments, the methods described herein further comprise obtaining a sample of epithelial cells from a subject; determining the level of P-selectin expression in the sample; comparing the level of P-selectin expression to a reference value, wherein a level of P-selectin in comparison to the reference value is indicative of the presence of a condition associated with aberrant epithelial cell proliferation. In this context, it is only subjects identified as having a condition associated with aberrant epithelial cell proliferation that is treated for the condition with an effective amount of an agent that inhibits P-selectin expression or activity.

The skilled person would appreciate that the sample of epithelial cells described herein may be obtained from a subject using a number of different techniques. Suitable techniques contemplated by the present disclosure include excisional biopsy, incisional biopsy, core biopsy, needle aspirational biopsy or liquid biopsy.

The inhibition of P-selectin activity is dependent, at least in part, on the level of P-selectin expression in the epithelial cell. The skilled person would appreciate that determining the level of P-selectin in accordance with the present disclosure may be performed using a variety of techniques known in the art. In exemplary embodiments, the level of P-selectin may be determined by determining the level of P-selectin gene expression. Suitable methods for determining the level of P-selectin gene expression include northern blots, polymerase chain reaction (PCR)-based methods, RNA sequencing (RNAseq), targeted sequencing and NanoString gene expression analysis. In other exemplary embodiments, the level of P-selectin may be determined by determining the level of P-selectin protein expression. Suitable methods for determining the level of P-selectin protein expression include enzyme-linked immunosorbent assay (ELISA), radioimmunoassay (RIA), western blotting and immunohistochemistry.

In some instances, the methods disclosed herein before comprise a comparative step (i.e., to identify whether the subject has a condition associated with aberrant epithelial cell proliferation) in which the level of P-selectin compared to a reference value. The term "reference value" as used herein refers to a predetermined level of expression of P-selectin that is representative of the level of expression of P-selectin is a particular cohort or population of subjects (i.e., normal healthy subjects, subjects that have never been diagnosed with a condition associated with aberrant epithelial cell proliferation). In an illustrative example, the comparison may be carried out using a reference value that is representative of a known or predetermined level of expression of P-selectin in a reference sample or a plurality of reference samples, which is associated with the absence of a condition associated with aberrant epithelial cell proliferation.

The reference value may be represented as an absolute number, or as a mean value (e.g., mean+/− standard deviation, such as when the reference value is derived from (i.e., representative of) a population of individuals. The reference value may be equal to or not significantly different from the level of expression of P-selectin in a sample population representative of subjects who have never been diagnosed with a condition associated with aberrant epithelial cell proliferation. Thus, a level of expression of P-selectin in a sample of epithelial cells from a test subject that is greater than the reference value is indicative of a condition associated with aberrant cell proliferation in the test subject. Conversely, a level of expression of P-selectin in a sample of epithelial cells from a test subject that is equal to or less than the reference value indicates that the test subject does not a condition associated with aberrant epithelial cell proliferation.

Whilst persons skilled in the art would understand that using a reference value that is derived from a sample population of individuals is likely to provide a more accurate representation of the level of expression in that particular population (e.g., for the purposes of the methods and protocols disclosed herein), in some embodiments, the reference value can be a level of expression of P-selectin in an individual.

In exemplary embodiments, the methods for treating a condition associated with aberrant epithelial cell proliferation described hereinbefore further comprises administering to the subject an effective amount of a second agent that inhibits Rho-kinase expression and/or activity. Suitable agents that inhibit Rho-kinase expression and/or activity include but are not limited to Rho-kinase or ROCK inhibitors fasudil, ripasudil, RKI-1447, Y-27632, GSK429286A and Y-301141).

Administration

The agent that inhibits P-selectin expression and/or activity according to the present disclosure may be administered as a therapeutic treatment (e.g., the subject has received at least one dose of adjunct chemotherapy or at least one radiation treatment). Those skilled in the art will appreciate that the methods, uses and compositions of the present disclosure may also be employed in combination with other therapies and treatments. For example, the agent that inhibits P-selectin expression and/or activity may be administered in combination with, for example, chemotherapy and radiation therapy (i.e., adjunct therapy).

It is well known that chemotherapy and radiation therapy target rapidly dividing cells and/or disrupts the cell cycle or cell division. These treatments may be offered as part of the treatment or prevention of a condition associated with aberrant epithelial cell proliferation, aiming either at slowing its progression or reversing the symptoms of the condition by means of a curative treatment. Thus, in some embodiments, the method further comprises a therapy or that employs one or more other chemotherapeutic agents. Suitable chemotherapeutic agents will be known to persons skilled in the art. Examples include cytostatic agents and cytotoxic agents. Examples of cytostatic agents include (1) microtubule-stabilizing agents such as taxanes, paclitaxel, docetaxel, epothilones and laulimalides; (2) kinase inhibitors, illustrative examples of which include Iressa®, Gleevec, Tarceva™, (Erlotinib HCl), BAY-43-9006, inhibitors of the split kinase domain receptor tyrosine kinase subgroup (e.g., PTK787/ZK 222584 and SU11248); (3) receptor kinase targeted antibodies, which include, but are not limited to, Trastuzumab (Herceptin®), Cetuximab (Erbitux®), Bevacizumab (Avastin™), Rituximab (Ritusan®), Pertuzumab (Omnitarg™); (4) mTOR pathway inhibitors, illustrative examples of which include rapamycin and CCI-778; (5) Apo2L/Trail, anti-angiogenic agents such as endostatin, combrestatin, angiostatin, thrombospondin and vascular endothelial growth inhibitor (VEGI); (6) antineoplastic immunotherapy vaccines, representative examples of which include activated T-cells, non-specific immune boosting agents (i.e., interferons, interleukins); (7) antibiotic cytotoxic agents such as doxorubicin, bleomycin, dactinomycin, daunorubicin, epirubicin, mitomycin and mitozantrone; (8) alkylating agents, illustrative examples of which include Melphalan, Carmustine, Lomustine, Cyclophosphamide, Ifosfamide, Chlorambucil, Fotemustine, Busulfan, Temozolomide and Thiotepa; (9) hormonal antineoplastic agents, non-limiting examples of which include Nilutamide, Cyproterone acetate, Anastrozole, Exemestane, Tamoxifen, Raloxifene, Bicalutamide, Aminoglutethimide, Leuprorelin acetate, Toremifene citrate, Letrozole, Flutamide, Megestrol acetate and Goserelin acetate; (10) gonadal hormones such as Cyproterone acetate and Medoxyprogesterone acetate; (11) antimetabolites, illustrative examples of which include Cytarabine, Fluorouracil, Gemcitabine, Topotecan, Hydroxyurea, Thioguanine, Methotrexate, Colaspase, Raltitrexed and Capicitabine; (12) anabolic agents, such as Nandrolone; (13) adrenal steroid hormones, illustrative examples of which include Methylprednisolone acetate, Dexamethasone, Hydrocortisone, Prednisolone and Prednisone; (14) neoplastic agents such as Irinotecan, Carboplatin, Cisplatin, Etoposide and Dacarbazine; and (15) topoisomerase inhibitors, illustrative examples of which include topotecan and irinotecan.

Examples of cytotoxic agents include sertenef, cachectin, ifosfamide, tasonertnin, lonidamine, carboplatin, altretamine, prednimustine, dibromodulcitol, ranimustine, fotemustine, nedaplatin, oxaliplatin, temozolomide (TEMODAR™ from Schering-Plough Corporation, Kenilworth, N.J.), cyclophosphamide, heptaplatin, estramustine, improsulfan tosilate, trofosfamide, nimustine, dibrospidium chloride, pumitepa, lobaplatin, satraplatin, profiromycin, cisplatin, doxorubicin, irofuiven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diatnine-platinum(II)]bis[diamine(chloro)platinum(II)] tetrachloride, diarizidinylspermine, arsenic trioxide, 1-(11-dodecyl amino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deansino-3'-morpholino-13-deoxo-10-hydroxycarminomycin, annamycin, galarubicin, elinafide, MEN10755, 4-demethoxy-3-deamino-3-aziddinyl-4-methylsulphonyl-daunombicin (see International Publication WO 00/50032), methoxtrexate, gemcitabine, and mixture thereof.

In another embodiment, the methods as herein described may be performed in combination with radiotherapy including, for example, conformal external beam radiotherapy (10-100 Grey given as fractions over 4-8 weeks), either single shot or fractionated, high dose rate brachytherapy, permanent interstitial brachytherapy, systemic radio-isotopes (e.g., Strontium 89). In illustrative examples of this type, the radiotherapy can be administered in combination with a radiosensitizing agent. Examples of radiosensitizing agents include, but are not limited to, efaproxiral, etanidazole, fluosol, misonidazole, nimorazole, temoporfin and tirapazamine.

For combination therapies, each component of the combination may be administered at the same time, or sequentially in any order, or at different times, so as to provide the desired effect. When administered separately, it may be preferred for the components to be administered by the same route of administration, although it is not necessary for this to be so. Alternatively, the components may be formulated together in a single dosage unit as a combination product.

The agents or compositions of the present invention and, optionally, any adjunct treatment(s), may be administered on a routine schedule. Alternatively, the agents or compositions may be administered as symptoms arise. A "routine schedule", as used herein, refers to a predetermined designated period of time. The routine schedule may encompass periods of time which are identical or which differ in length, as long as the schedule is predetermined. For instance, the routine schedule may involve administration of an agent that inhibits P-selectin expression and/or activity in epithelial cells and an agent that inhibits Rho-kinase expression and/or activity (sequentially or in combination) on a daily basis, every two days, every three days, every four days, every five days, every six days, a weekly basis, a monthly basis or any set number of days or weeks there-between, every two months, three months, four months, five months, six months, seven months, eight months, nine months, ten months, eleven months, twelve months, etc. Alternatively, the predetermined routine schedule may involve administration of the agent(s) on a daily basis for the first week, followed by a monthly basis for several months, and then every three months after that. Any particular combination would be covered by the routine schedule as long as it is determined ahead of time that the appropriate schedule involves administration on a certain day.

Compositions

Also disclosed herein are pharmaceutical compositions suitable for the treatment of conditions associated with aberrant epithelial cell proliferation.

Accordingly, embodiments of the present disclosure provide a pharmaceutical composition comprising an agent for inhibiting P-selectin expression and/or activity in epithelial cells for use in inhibiting epithelial cell proliferation in a subject in need thereof.

The pharmaceutical composition may comprise a single agent, or a plurality of agents. For example, the composition can comprise (i) an agent that inhibits P-selectin gene expression in epithelial cells (as herein described), (ii) an agent that inhibits P-selectin activity in epithelial cells, and optionally (c) an agent that inhibits Rho-kinase expression and/or activity (as herein described). In an embodiment, the composition comprises (i) an agent that inhibits P-selectin gene expression in epithelial cells (as herein described), (ii) an agent that inhibits P-selectin activity in epithelial cells, and (iii) an agent that inhibits Rho-kinase expression and/or activity (as herein described). In another embodiment, the composition comprises (i) an agent that inhibits P-selectin gene expression in epithelial cells (as herein described) and (ii) an agent that inhibits P-selectin activity in epithelial cells. In another embodiment, the composition comprises (i) an agent that inhibits P-selectin activity in epithelial cells, and (iii) an agent that inhibits Rho-kinase expression and/or activity (as herein described). In another embodiment, the composition comprises (i) an agent that inhibits P-selectin gene expression in epithelial cells, and (ii) an agent that inhibits Rho-kinase expression and/or activity (as herein described).

In exemplary embodiments, the pharmaceutical composition comprises a pharmaceutically acceptable carrier. The pharmaceutical composition may also include an ancillary or additional medicament. Typically, the agent(s) will be present in the pharmaceutical composition in an amount that will provide an effective amount, when administered to the subject, for preventing or treating the condition associated with aberrant endothelial cell proliferation (e.g., cancer). The effective amount for treating the condition is that amount which completely or partially inhibits epithelial cell proliferation in the subject, prevents the worsening of, or treats the established existence of, the condition. In some instances, the effective amount for preventing or treating the condition completely or partially prevents or treats one or more clinical symptoms of that condition.

In addition to clinical outcomes measured in terms of physiology, in vitro assays measuring epithelial cell-derived factors may also be used in determining a dosage amount that will provide an in vivo effective amount of an agent. Such methods will be known to persons skilled in the art. In practice, such measurements (particularly for cell counts)

may be made by an automated cell counting devices designed for that purpose, or they may be performed manually. Manual counts may be more accurate than automated counts when cell counts are particularly low.

The pharmaceutical composition of the present invention may be formulated and/or administered in pharmaceutically acceptable solutions, which may contain pharmaceutically acceptable concentrations of salt, buffering agents, preservatives, compatible carriers, adjuvants, and optionally other therapeutic ingredients. Depending on the specific conditions being treated or prevented, such compositions may be administered or formulated for administration systemically or locally. Techniques for formulation and administration may be found in "Remington's Pharmaceutical Sciences", Mack Publishing Co., Easton, Pa., latest edition". Suitable routes may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections. For injection, the agent(s) may be formulated in aqueous solutions, such as physiologically compatible buffers (e.g., Hanks' solution, Ringer's solution, or physiological saline buffer). For transmucosal administration, penetrants appropriate to the barrier to be permeated are used in the formulation. Such penetrants will be known to persons skilled in the art.

The compositions may also be formulated using pharmaceutically acceptable carriers well known to persons skilled in the art into dosages suitable for oral administration. Such carriers enable the compounds to be formulated in dosage forms such as tablets, pills, capsules, liquids, gels, syrups, slurries, suspensions and the like, for oral ingestion by a patient to be treated. These carriers may be selected from sugars, starches, cellulose and its derivatives, malt, gelatine, talc, calcium sulphate, vegetable oils, synthetic oils, polyols, alginic acid, phosphate buffered solutions, emulsifiers, isotonic saline, and pyrogen-free water.

Pharmaceutical compositions suitable for use in accordance with the present invention include compositions wherein the active ingredient(s) (i.e., agent(s)) are present in an amount to achieve its intended purpose following administration. The dose of drug administered to a patient should be sufficient to effect a beneficial response in the patient over time; namely, a reduction in epithelial cell proliferation or symptoms associated therewith. The quantity of agent(s) to be administered may depend on the subject to be treated, inclusive of the age, sex, weight and general health condition thereof. In this regard, precise amounts of agent(s) for administration may depend on the judgment of the practitioner. In determining the effective amount of the agent(s) to be administered in the treatment or prophylaxis of the condition, the physician may evaluate tissue levels of epithelial cell-derived products (e.g., proteins released by activated or proliferating epithelial cells) as a surrogate marker of the degree of epithelial cell proliferation in the subject. In any event, those of skill in the art may readily determine suitable dosages of the agents of the present invention.

Pharmaceutical compositions formulated for parenteral administration include, but are not limited to, aqueous solutions of the agents in water-soluble form. Additionally, suspensions of the agents may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilisers or agents which increase the solubility of the compounds to allow for the preparation of highly concentrated solutions.

Pharmaceutical compositions formulated for oral administration may be prepared by combining the agent(s) with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatine, gum tragacanth, methyl cellulose, hydroxypropylmethyl-cellulose, sodium carboxymethylcellulose, or polyvinylpyrrolidone (PVP). If desired, disintegrating agents may be added, such as the cross-linked polyvinyl pyrrolidone, agar, or alginic acid or a salt thereof such as sodium alginate. Such compositions may be prepared by any of the methods of pharmacy but all methods include the step of bringing into association one or more agents as herein described with the carrier which constitutes one or more necessary ingredients. In general, the pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Dragee cores are provided with suitable coatings. For this purpose, concentrated sugar solutions may be used, which may optionally contain gum arabic, talc, polyvinyl pyrrolidone, carbopol gel, polyethylene glycol, or titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions that can be used orally include push-fit capsules made of gelatine, as well as soft, sealed capsules made of gelatine and a plasticizer, such as glycerol or sorbitol. The push-fit capsules can contain the agent(s) in admixture with filler such as lactose, binders such as starches, or lubricants such as talc or magnesium stearate and, optionally, stabilisers. In soft capsules, the agent(s) may be dissolved or suspended in suitable liquids, such as fatty oils, liquid paraffin, or liquid polyethylene glycols. In addition, stabilisers may be added.

Dosage forms of the agent(s) of the present invention may also include injecting or implanting controlled releasing devices designed specifically for this purpose or other forms of implants modified to act additionally in this fashion. Controlled release of the agent(s) may be effected by coating the same, for example, with hydrophobic polymers including acrylic resins, waxes, higher aliphatic alcohols, polylactic and polyglycolic acids and certain cellulose derivatives such as hydroxypropylmethyl cellulose. In addition, controlled release may be effected by using other polymer matrices, liposomes or microspheres.

The agent(s) of the present invention may also be provided as salts. Pharmaceutically compatible salts may be formed with many acids, including hydrochloric, sulphuric, acetic, lactic, tartaric, malic, succinic, etc. Salts tend to be more soluble in aqueous or other protonic solvents that are the corresponding free base forms.

For any compound used in accordance with the methods of the present invention, the effective therapeutic dose may be estimated initially from an in vitro assay (e.g., cell culture assays). For example, a dose can be formulated in an animal model to achieve a circulating concentration range that includes the IC50 as determined in cell culture (e.g., the concentration of an active agent, which achieves a half-maximal inhibition of endothelial cell proliferation). Such information can be used to more accurately determine a useful therapeutic or prophylactic dose for in vivo use.

Toxicity and therapeutic or prophylactic efficacy of such agents can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic or prophylactic effects is the therapeutic index and it can be expressed as the ratio LD50/ED50. The data obtained from cell culture assays and/or animal studies may then be used to formulate a range of dosage for use in humans. The dose of such compounds may reside within a range of circulating concentrations that include the ED50 with little or no toxicity. The dose may vary within this range depending upon the dosage form employed and the route of administration utilized. The exact formulation, route of administration and dosage can be chosen by the individual physician in view of the patient's condition. (See for example Fingl et al., 1975, in "The Pharmacological Basis of Therapeutics", Ch. 1 p 1).

Dosage amount and interval may be adjusted individually to provide plasma levels of the agent(s) that are sufficient to inhibit endothelial cell proliferation in vivo. Dosages for systemic administration may range from 1-2000 mg/day, commonly from 1-250 mg/day, and typically from 10-150 mg/day. Stated in terms of patient body weight, usual dosages may range from 0.02-25 mg/kg/day, commonly from 0.02-3 mg/kg/day, typically from 0.2-1.5 mg/kg/day. Stated in terms of patient body surface areas, dosages may range from 0.5-1200 mg/m$^2$/day, commonly from 0.5-150 mg/m$^2$/day, typically from 5-100 mg/m$^2$/day.

Alternatively, one may administer the agent(s) in a local rather than systemic manner, for example, via injection of the compound directly into a tissue, which may be subcutaneous or omental tissue, often in a depot or sustained release formulation. Furthermore, one may administer the agent(s) in a targeted drug delivery system, for example, in a liposome coated with tissue-specific antibody. The liposomes will be targeted to and taken up selectively by the tissue. In cases of local administration or selective uptake, the effective local concentration of the agent(s) may not be related to plasma concentration.

All publications mentioned in this specification are herein incorporated by reference. The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

It will be appreciated by persons skilled in the art that numerous variations and/or modifications may be made to the present disclosure without departing from the spirit or scope of the disclosure as broadly described. The present embodiments are, therefore, to be considered in all respects as illustrative and not restrictive.

The present disclosure will now be further described in greater detail by reference to the following specific examples, which should not be construed as in any way limiting the scope of the disclosure.

EXAMPLES

Materials and Methods

A. Maintenance and Culture of HCE-T Cells

The human corneal epithelial cell line HCE-T (Riken Cell Bank Cat. No. RCB2280, Lot No. 002) was maintained in Dulbecco's modification of Eagle's medium with high glucose (Life Technologies) supplemented with 10% (v/v) fetal bovine serum (FBS; Thermo Scientific), 2.5 mM L-glutamine (Life Technologies) and antibiotics (1% v/v dilution of penicillin/streptomycin solution; Life Technologies). The HCE-T were routinely seeded at 1×10$^5$ cells per 75 cm$^2$ culture flask and fed with fresh medium every 3 days until approximately 80-90% confluent. The incubator was maintained at 37° C. with 5% CO$_2$ in air. Cultures were passaged using trypsin/EDTA (Life Technologies). For immunocytochemistry, samples of HCE-T were cultivated to approximately 80-90% confluency in 24-well culture plates.

B. Immunocytochemistry for P-Selectin

Prior to staining, each culture was fixed by treatment for 20 minutes in 10% (v/v) neutral buffered formalin (3.7% formaldehyde), washed twice in phosphate buffered saline, incubated at 37° for 30 minutes in PBS containing 2% (v/v) normal goat serum (NGS), then washed twice in PBS. Staining for P-selectin was subsequently performed using a mouse monoclonal antibody to human P-selectin (Clone 9E1, R & D Systems). The primary antibody was prepared as a 0.5 mg/mL stock in PBS and stored in 10 aliquots at −80° C. Staining was performed for 1 hour at 37° C. using a 1:25 dilution of primary antibody in PBS supplemented with 1% NGS. A negative control was always performed by excluding this primary antibody incubation step. After washing three times in PBS, bound primary antibody was detected using an Alexa 488-conjugated goat-anti-mouse IgG (Molecular Probes) applied for 1 hour at 37° C. as a 1:100 dilution in PBS supplemented with 1% NGS. Some cultures were counterstained to display cell nuclei by incubation for 1 hour in HEPES buffered saline (20 mM HEPES/ 0.85% w/v NaCl) containing 2 µg/mL Hoechst 33342 nuclear stain (Invitrogen/Molecular Probes). Stained cultures were examined using a Nikon TE2000-U microscope equipped with a 10×/0.3 NA Plan Fluor phase contrast objective lens and a CoolSNAP ES cooled CCD camera (Photometrix).

C. Establishment and Cultivation of Primary Corneal-Limbal Epithelial Cells

Cultures of non-transformed human corneal epithelial cells were established from either enzymatically-dissociated sample of corneal-scleral tissue or from pieces of intact corneal limbus seeded into culture dishes (i.e., explant method). In either case, corneal tissue from cadaveric donors was used. Each tissue sample was acquired with consent and ethics approval our HREC Approval No. 0800000807) in the form of either surgical cut-offs or intact corneas that had been rejected by the eye bank (e.g., poor endothelial cell density).

For dissociated cultures, washed tissue samples were cut into quarters before being incubated for 1 hour at 37° C. in 0.25% (w/v) Dispase solution (Life Technologies). Epithelial tissue was subsequently harvested from the limbus and peripheral cornea by scraping with a pipette tip, then dissociated by digestion in 0.05% Trypsin/0.02% EDTA (Sigma) for 5 minutes at 37° C. The resulting cell suspension was washed and resuspended in complete culture medium. The culture medium consisted of 1:3 mixture of DMEM and Hams F12 (Life Technologies) supplemented with 10% FBS, non-essential amino acids (NEAA), 10 mM L-glutamine, penicillin (100 IU/mL)/Streptomycin (100 µg/mL), 10 ng/mL epidermal growth factor (EGF), 3,3,5-triodo-L-thyronine sodium salt (T3), 180 µM adenine, 5 µg/mL transferrin, 0.4 µg/mL hydrocortisone, 1 µg/mL insulin and $10^{-5}$ M isoproterenol. The entire cell suspension derived from one corneal limbus was then seeded into a 25 cm² culture flask containing a near confluent layer of gamma irradiated (2×25 Gy) murine 3t3 feeder cells.

To initiate cultures from whole tissue, each well of a 6-well culture plate (approximately 6×10 cm²) was initially filled with 2 mL, of 100% FBS and incubated for at least 30 minutes at 37° C. After removing most of the serum, a 2-mm trephine punch was used to excise buttons from intact and downward facing pieces of washed corneal-scleral limbus. Each tissue button was then dispensed into the centre of a serum-treated well by depressing the plunger on the trephine punch. The orientation of each dispensed tissue button was checked to ensure that the epithelial side was in contact with the serum-treated culture plastic. Each plate containing up to 6 pieces of tissue (and a thin film of serum) was then placed into the tissue culture incubator to facilitate attachment. After approximately 1 hour, a small volume (~250 µL) of complete culture medium was carefully dispensed around each explant, taking care not to cause detachment. Additional medium was progressively added over the next 24-hours up to a final volume of about 2 mL. Over subsequent days, each p0 culture was routinely monitored for evidence of epithelial outgrowth until a confluent sheet measuring approximately 2-3 cm² had been achieved (approximately 1-2 weeks).

Treatment of Cells with siRNA siRNA targeting P-selectin was purchased as Mission esiRNA Human SELP (esirnal) (Sigma-Aldrich Cat. No. EF111039631-50UG). HiPerFect transfection reagent was used (Qiagen, Cat. No. 301704). For optimal transfection conditions, the cells were plated out the day before transfection such that they attained 30-50% confluency in full growth medium in the absence of 3T3 feeder cells. A 600 nM solution of each siRNA concentrate was prepared separately in serum-free medium. The HiPerfect transfection reagent was added to the siRNA concentrates at the ratio of 4 µL of HiPerFect transfection reagent per 100 µL of siRNA concentrate. Each sample was mixed using a Vortex for 10 seconds, before standing at room temperature for 10 min to form the transfection complex. The transfection complex solution was subsequently added slowly to the cultures whilst gently rocking the culture plate such that the final siRNA concentration reached approximately 100 nM. Cells were grown for three days following the addition of the transfection reagent.

E. Quantitative PCR (RT-qPCR)

Relative mRNA levels of P-selectin were analysed by quantitative (real time) PCR. Total RNA was isolated using the phenol-chloroform extraction method using TRIsure Reagent (Bioline) according to the manufacturer's instructions. cDNA was synthesised from 2 µg RNA using random hexamer primers and RevertAid Reverse Transcriptase (RT) and amplified using primers for P-selectin and β-actin as a control.

TABLE 1

Primers used for RT-qPCR

| Primer | Primer sequence in the 5'-3' orientation |
|---|---|
| Human β-actin forward | CAT GTA CGT TGC TAT CCA GGC (SEQ ID NO: 1) |
| Human β-actin reverse | CTC CTT AAT GTC ACG CAC GAT (SEQ ID NO: 2) |
| Human P-selectin forward | CTG TTA CCC TGG ATT CTA TGG GC (SEQ ID NO: 3) |
| Human P-selectin reverse | GCT GCA CTG CGA GTT AAA AGA G (SEQ ID NO: 4) |

Quantitative PCR was performed using cDNA samples that had been prepared from 2 µg total RNA from each cell culture under investigation. Each reaction consisted of 2 µL, cDNA (diluted 1:10 in water), 2 µL forward primer (5 µM), 2 µL reverse primer (5 µM), 4 µL water and 10 µL, SYBR green mixture. Reactions were performed in duplicate in a 96-well plate under the following cycling conditions: a pre-incubation step at 95° C. for 10 mins, followed by two step amplification: 45 cycles of 95° C. for 10 sec, 62° C. for 10 sec and 72° C. for 10 sec; 1 cycle of 95° C. for 10 sec, 65° C. for 60 sec and 97° C. for 1 sec. β-actin was used as an internal reference for each test sample and target gene expression was reported as a ratio of expression after comparison with β-actin expression.

F. Analysis of Metabolic Activity (MTT Assay)

Measurement of mitochondrial enzyme activity by MTT conversion was utilised as an indirect assessment of metabolic and proliferative activity. MTT reagent was prepared by diluting the MTT stock solution (5 mg/mL) 1:10 in PBS (i.e., to a final concentration of 0.5 mg/mL MTT). Prior optimization of growth conditions (seeding density and duration in culture) was conducted to ensure sub-confluency at the time of measurement. For example, a seeding density of 10,000 cells per cm² and a culture period of 48-hours were routinely used. On the day of analysis, the culture medium was removed from each well and replaced with a fixed volume (0.5 mL per well of a 24 well plate) of MTT solution and incubated at 37° C. for 40 minutes. The MTT reagent was subsequently removed and the formazan product eluted by adding a fixed volume (300 µL per well of a 24 well plate) of acidified isopropanol (24.6 µL of concentrated HCL in 20 mL of isopropanol) to each well for approximately 5 minutes, 150 µL of the eluted stain from each well was then transferred into corresponding wells of a 96 well plate. The optical density was measured using a plate reader at 550 nm (background 620 nm).

G. Endothelial Cell Proliferation Analysis

Microvascular endothelial cells (MEC) were cultured in MEC Culture Medium comprising 500 mL of MCDB-131 media containing 5 mL of 1M L-Glutamine, 5 Penicillin (10,000 IU/mL)/Streptomycin (10,000 ug/mL), 10% v/v foetal calf serum (FCS), 0.5 mL of 1 mg/mL hydrocortisone (Hc) and 0.5 mL of 10 ug/mL epidermal growth factor (EGF).

Spent culture media was removed and the flask rinsed with 5 mL of phosphate buffered saline (without magnesium or calcium; PBSA). After 30 seconds, the PBSA was removed and 5 mL of 0.02% EDTA/0.05% trypsin reagent was added to the cells. The flask was then incubated at 37°

C. for 5-8 minutes. The cells were then dislodged from the flask, removed and added to a 50 mL centrifuge tube containing an equal volume of culture media to neutralize the 0.02% EDTA/0.05% trypsin reagent. This tube was then centrifuged at 100 g for 5 minutes to form a pellet of cells. The supernatant was removed and the pellet of cells resuspended. The diluted cells were split 1:3 into new flasks containing culture media. The flasks were then placed in a humidified CO2 (5%) incubator at 37° C. until the cells were approximately 80% confluent. The process was repeated weekly. For the purpose of serum-free culturing, the MEC and LEC cells were serum starved by incubating them in serum-free MCDB-131 medium (Gibco/Life Technologies) for 12 hours. Limbal epithelial cells (LEC) were cultured in a similar manner to MEC in LEC Culture Medium comprising 500 mL of DMEM/F12 media containing 5 mL of 1M L-Glutamine, 5 mL of Pen (10,000 IU/mL)/Strep (10, 000 ug/mL) and 10% FCS (v/v).

Additional reagents used in these experiments are described below:
- 0.02% EDTA/0.05% trypsin reagent: 5 mL of 2% EDTA solution and 10 mL of thawed 2.5% trypsin solution were added to 485 mL of PBSA, 50 mL aliquots were dispensed into 50 mL centrifuge tubes and stored below −20° C.
- Pre-bound Collagen IV: 250 µL of Collagen IV stock solution was added to the wells of a 24 well tissue culture plate and allowed to dry completely over night in a biohazard cabinet.
- Pre-bound Vitronectin: a vitronectin stock solution (2 mg/mL) was diluted in water to a final concentration of 5 µg/mL. 200 µL of this was added to wells of a 24-well plate and allowed to stand at 37° C. for 2 hours.
- Pre-bound P-selectin/PSGL-1: 100 µL of recombinant human P-selectin stock solution (100 µg/mL) was add to 1 mL of MCDB (including 0.1% bovine serum albumin; BSA) to give a final solution of approximately 10 µg/mL. 250 µL was then added to each well and allowed to stand at 37° C. for 2 hours.
- Pre-bound E-selectin: 10 µL of recombinant human E-selectin stock solution (10 mg/mL) was added to 1.1 mL of MCDB (with 0.1% BSA) to a final solution of give approximately 10 µg/mL. 250 µL of this final solution was then added to each well and allowed to stand at 37° C. for 2 hours.

Following binding of the above-mentioned pre-bound matrix constituents, culture plates were washed in phosphate buffered saline. The solution phase reagents (thrombin, heparin, antithrombin III, glucose and insulin) were then applied in serum-free MEC basal cell culture medium (MCDB-131) (or DMEM:F12 basal cell culture medium where LEC cells were under investigation), in the presence of glutamine, prior to the addition of cells (50,000 cells/well). Cells were serum-starved for a minimum of 12 hours prior to seeding.

All solution phase reagents (thrombin, antithrombin III, glucose) were added directly from stock into the culture media. Where two or more matrix constituents were pre-bound, the selectins were subsequently pre-bound.

In the experiments conducted, the cells were grown in 24-well plates. The negative control was represented by cells grown only in basal media. The positive control was represented by cells grown in basal media with FCS. In the case of MEC, the positive control media also included hydrocortisone and epidermal growth factor (EGG). The test media included basal media only (no FCS or growth factors) along with the reagent of interest.

Example 1

Epithelial Cells Express P-Selectin

Figure 2:
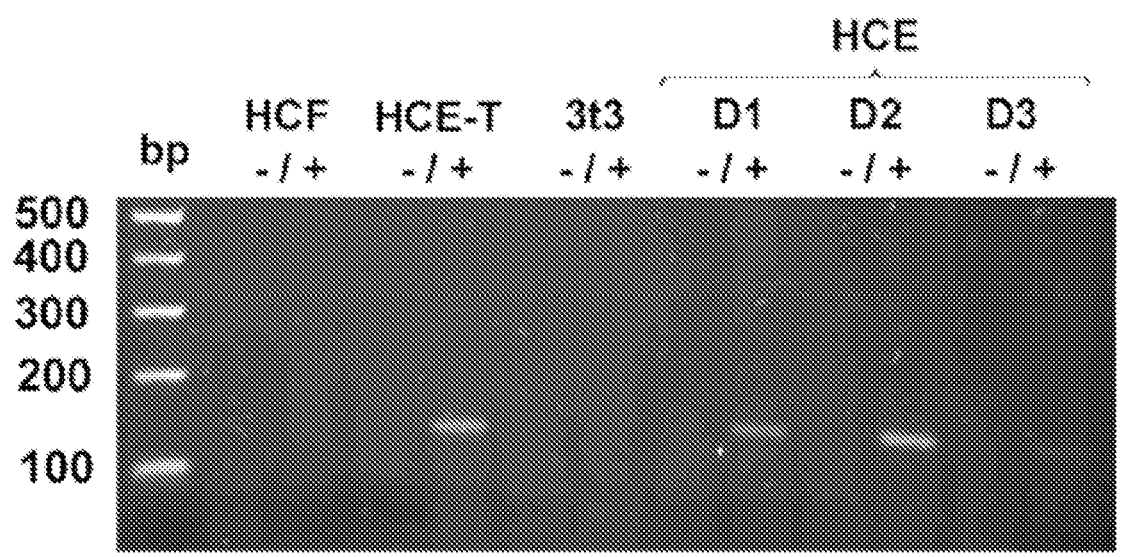
FIG. 2 is a photographic representation of P-selectin gene expression in human corneal epithelial cells. Messenger RNA was extracted from transformed human corneal-limbal epithelial cells (HCE-T) and non-transformed human corneal-limbal epithelial cells (HCE) derived from three unique tissue donors (D1, D2, D3). Negative/positive symbols indicate the absence/presence of reverse transcriptase. Additional controls consisted of non-transformed human corneal-limbal stromal cells (presumed fibroblasts; HCF) and murine 3t3 cells (both potential contaminants of HCE cultures).
Figure 3:
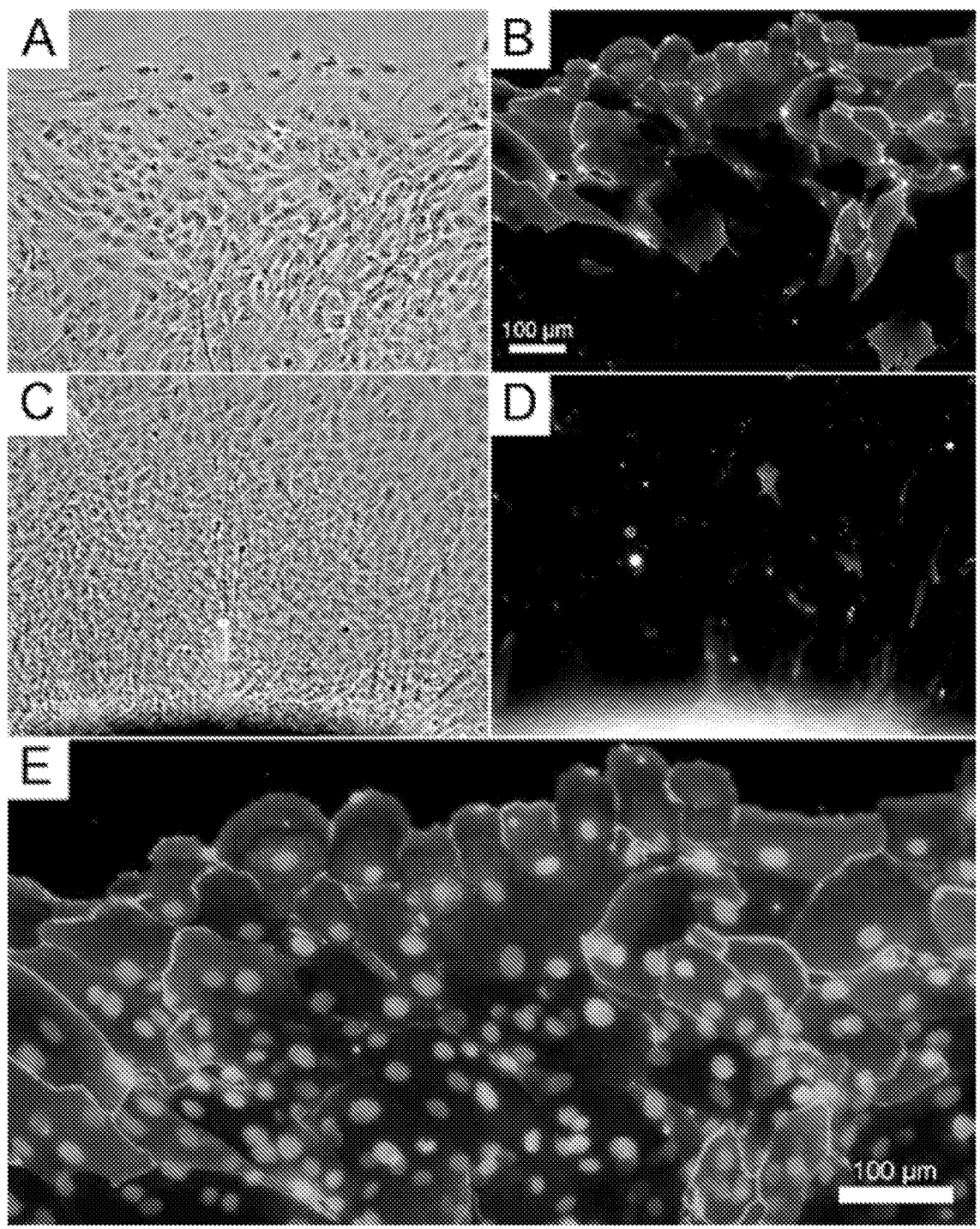
FIG. 3 is a photographic representation of primary human corneal cells expressing P-selectin. Staining of formalin-fixed cells is observed that the periphery of the expanding epithelial culture (A & B). In contrast, less staining is observed in cells located adjacent to the tissue explant (C & D). (E) 2-fold magnification of (B) in conjunction with Hoechst nuclear counter-stain (blue).

As shown in FIG. 1, P-selectin is expressed in corneal epithelial cells (SV40-immortalised cell line HCE-T). The majority of HCE-T cells displayed prominent immunostaining, particularly at cell-to-cell boundaries (FIG. 1D). In contrast, the technical negative control displayed minimal to no staining (FIG. 1B). Subsequent analysis of mRNA extracted from HCE-T cells by RT-PCR revealed a single reaction product with a size consistent with that expected or amplified P-selectin (FIG. 2). The PCR product was subsequently confirmed as human P-selectin by bi-directional sequencing performed at an independent testing laboratory (Australian Genome Research Facility, University of Queensland).

Since virally transformed cell lines, including HCE-T are known to display aberrant changes in gene expression (e.g., Yamasaki et al. (2009), *Investigative Opthahnology & Visual Science,* 50(2): 604-613), the expression of P-selectin was investigated in a culture of non-transformed corneal epithelial cells established from cadaveric human tissue. First passage cultures were immunostained for P-selectin, with heterogeneous staining observed. Similar to the transformed cells, staining in primary cells was also most strongly observed at cell-cell boundaries (FIG. 1F). Subsequent analysis by RT-PCR revealed faint to moderate intensity bands of a similar product size to that generated from HCE-T cells (FIG. 2). The identity of each PCR product was confirmed as human P-selectin by an independent testing facility as hereinbefore described.

Example 2

Figure 4:
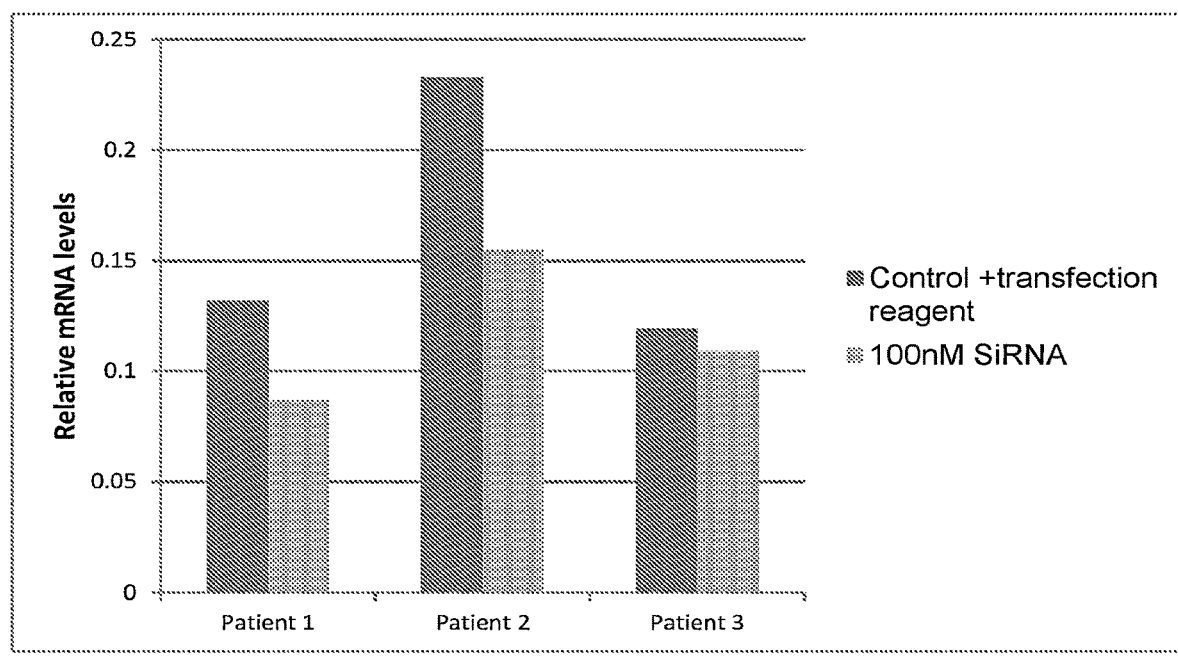
FIG. 4 shows that inhibition of P-selectin gene expression by 100 nM siRNA inhibits epithelial cell proliferation of primary cell lines derived from three different patients with cancer, when compared to the Control.

Inhibition of P-Selectin Gene Expression using siRNA Inhibits Epithelial Cell Proliferation Primary cultures of corneal-limbal epithelial cells displayed a dose-dependent decrease in MTT conversion when exposed to siRNA to P-selectin (FIG. 4), reflecting a reduction or inhibition of cell metabolism.

By contrast, treatment with transfection reagent alone had no significant effect on the metabolic response.

Figure 5:
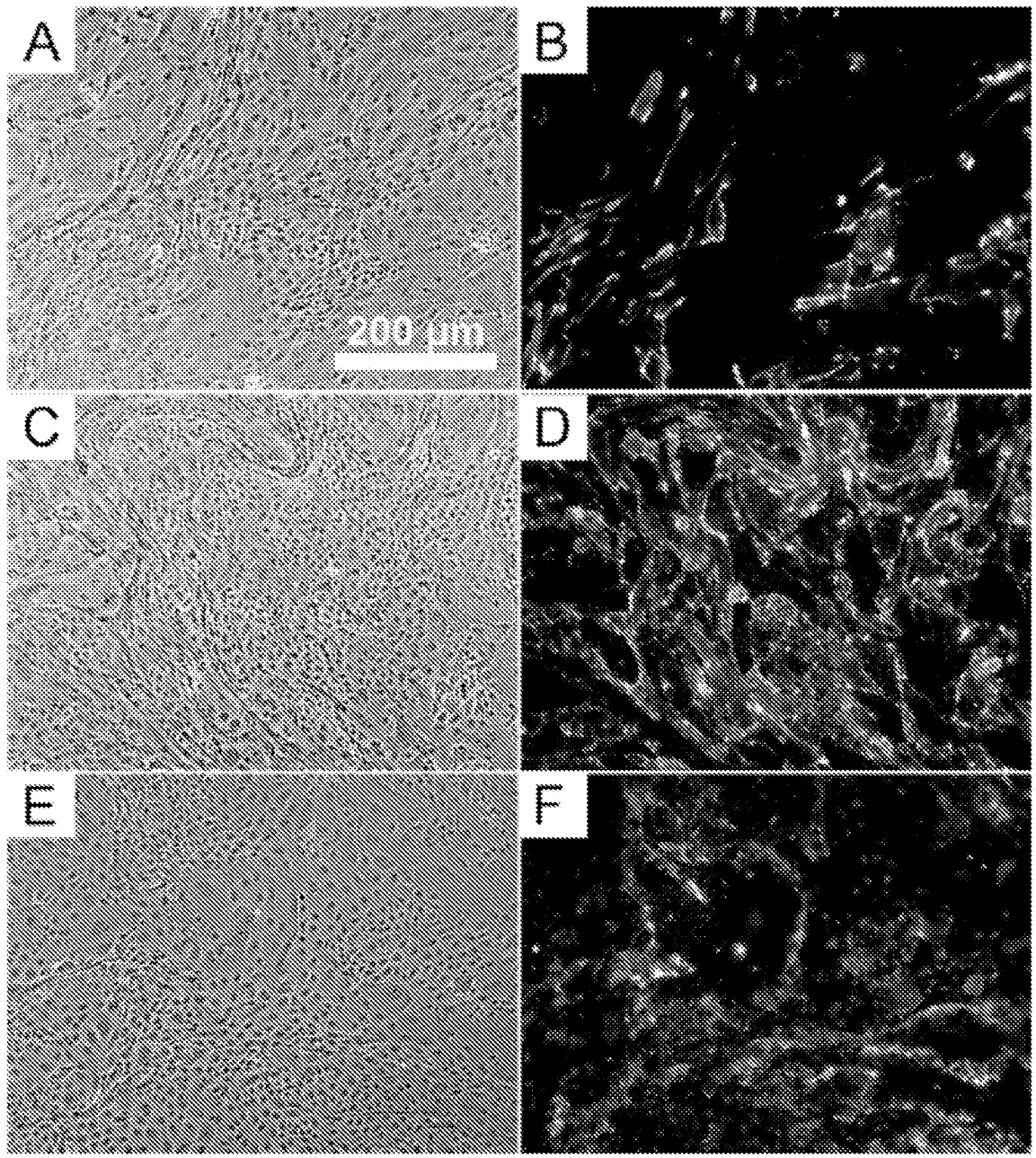
FIG. 5 is a photographic representation showing that P-selectin siRNA in combination with ROCK inhibitor abrogates Rho-kinase inhibitor-mediated epithelial cell proliferation and changes the cellular distribution of P-selectin, (A/B) Control culture in the absence of Y27632 or siRNA. (C/D) Culture treated with Y27632 alone. (E/F) Culture treated with both Y27632 and siRNA.
Figure 6:
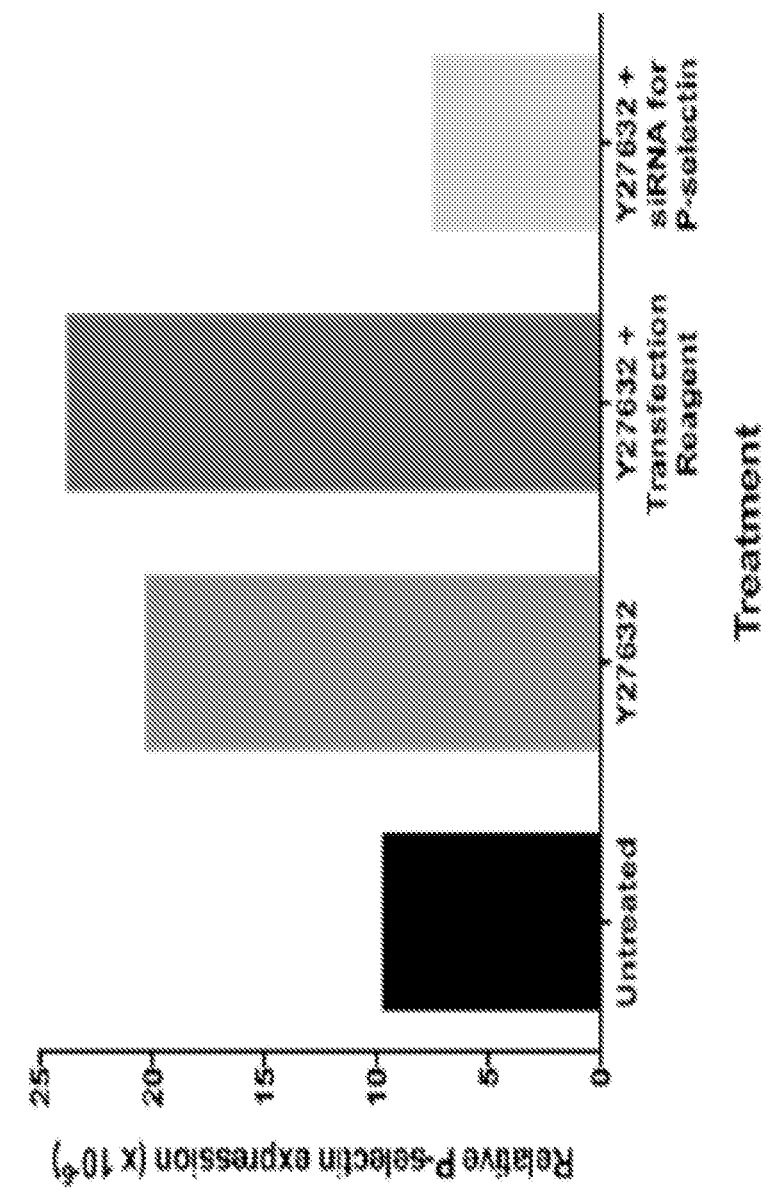
FIG. 6 shows P-selectin gene expression (mRNA) in the presence of P-selectin siRNA and Y27632. Reduced levels of P-selectin mRNA in the presence of P-selectin siRNA (100 nM) were confirmed by RT-qPCR for one donor culture. Expression is shown as relative to β-actin mRNA.

Primary cultures of corneal-limbal epithelial cells displayed a dose-dependent increase in MTT conversion (i.e., increase in cell proliferation) when treated with 40 µM of the ROCK inhibitor Y27632 (FIG. 5D). This increase in proliferation was abrogated by the inclusion of siRNA to P-selectin (FIG. 5F). The decrease in cell proliferation in the presence of siRNA to P-selectin was accompanied by a corresponding decrease in P-selectin relative to β-actin (FIG. 6). Less intense staining for P-selectin protein was also apparent by immunohistochemistry (FIG. 513). It is hypothesised that Y27632 selects for P-selectin expressing cells, thereby creating vulnerability to P-selectin inhibition in the selected cells to inhibit cell proliferation.

Example 3

P-Selectin Reduces Endothelial Cell Proliferation In Vitro

Figure 7:
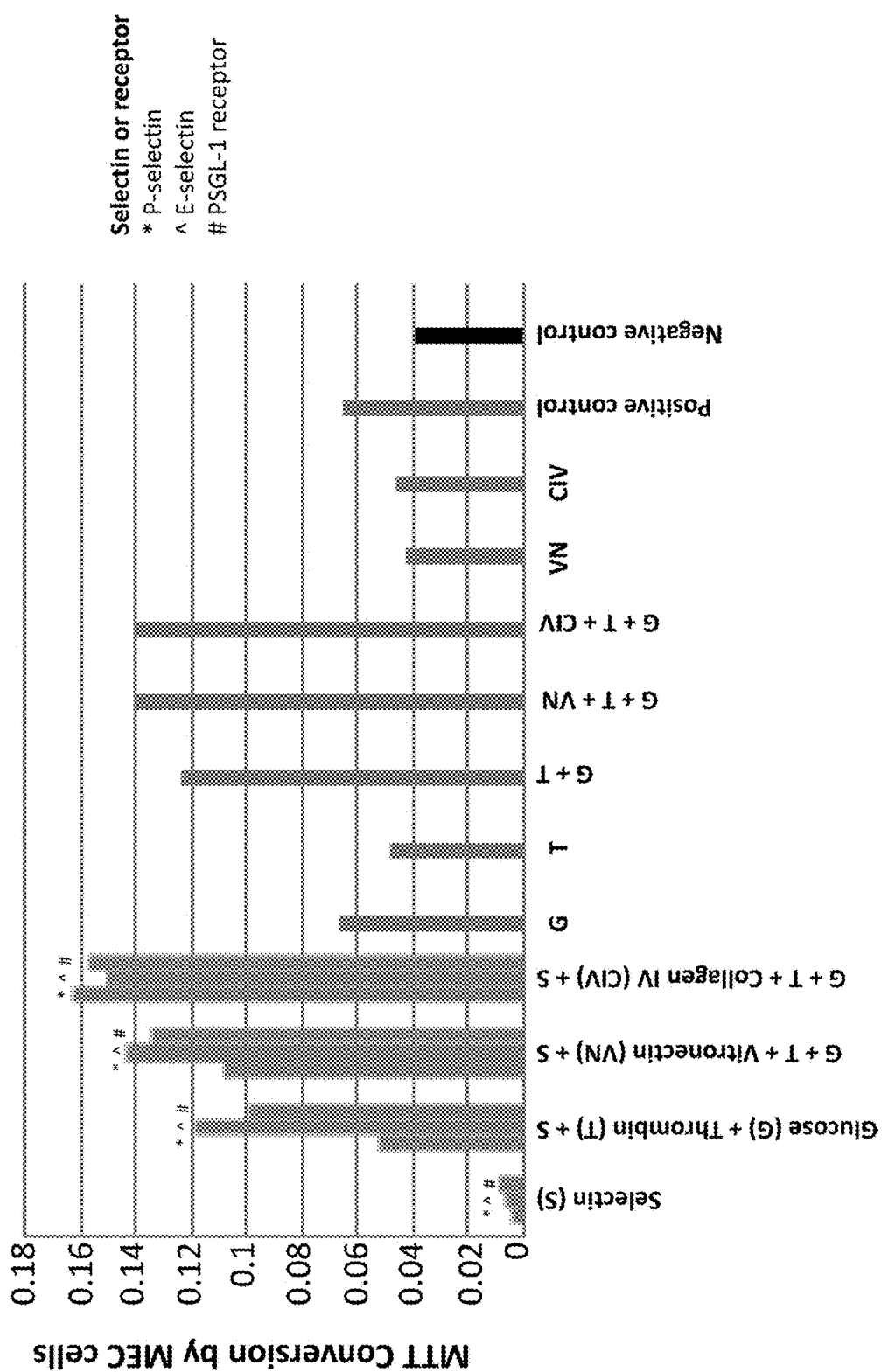
FIG. 7 shows the effect of pre-bound selectins and pre-bound selectin receptor (PSGL-1) on the metabolic response of microvascular endothelial cells (MEC) in vitro. The metabolic response by MEC to the selectins and their receptor was measured in the presence of thrombin (100 IU/mL), glucose (10 mg/mL), pre-bound vitronectin (VN) and pre-bound-collagen IV (CIV). Thrombin (T) and glucose (G) were added to the wells of a 24-well tissue culture plate prior to seeding of serum-starved cells (50,000/well), and cultivated for 2 days and an MTT assay performed.

As shown in FIG. 7, glucose alone marginally improved the proliferation of MEC. 100 IU/mL thrombin stimulated proliferation of MEC in synergy with glucose, exceeding the positive control. The presences of collagen IV, vitronectin or thrombin alone did not significantly stimulate proliferation of endothelium. Pre-bound selectins, in the absence of thrombin, inhibit proliferation of MEC. P-selectin reduced the thrombin-induced proliferation of MEC in the presence of glucose and in the absence of basement membrane proteins collagen IV and vitronectin.

Figure 8:
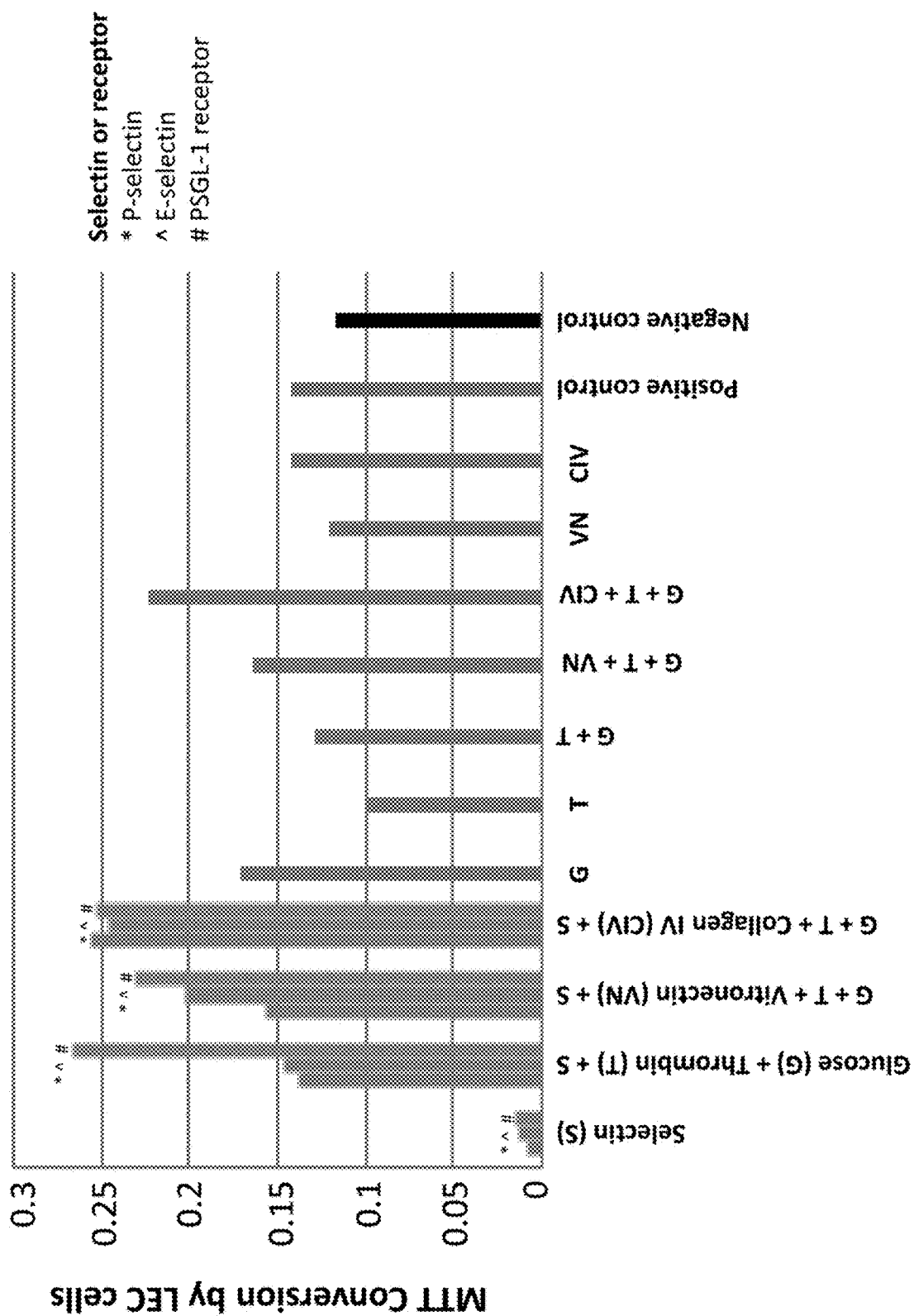
FIG. 8 shows the effect of pre-bound selectins and pre-bound selectin receptor (PSGL-1) on limbal epithelial cells (LEC). The metabolic response by LEC to the selectins and their receptor was measured in the presence of thrombin (T; 100 IU/mL), glucose (G; 10 mg/mL), pre-bound vitronectin (VN) and pre-bound-collagen IV (CIV). Thrombin and glucose were added to the wells of a 24-well tissue culture plate prior to seeding of serum-starved cells (50,000/well), and cultivated for 2 days and an MTT assay performed.

As shown in FIG. 8, glucose alone improved the proliferation of LEC. Thrombin, glucose, glucose with thrombin and vitronectin did not significantly stimulate proliferation of Pre-bound selectins, in the absence of thrombin, inhibited the proliferation of LEC. PSGL-1 stimulated thrombin induced proliferation of LEC in the presence of glucose.

Figure 9:
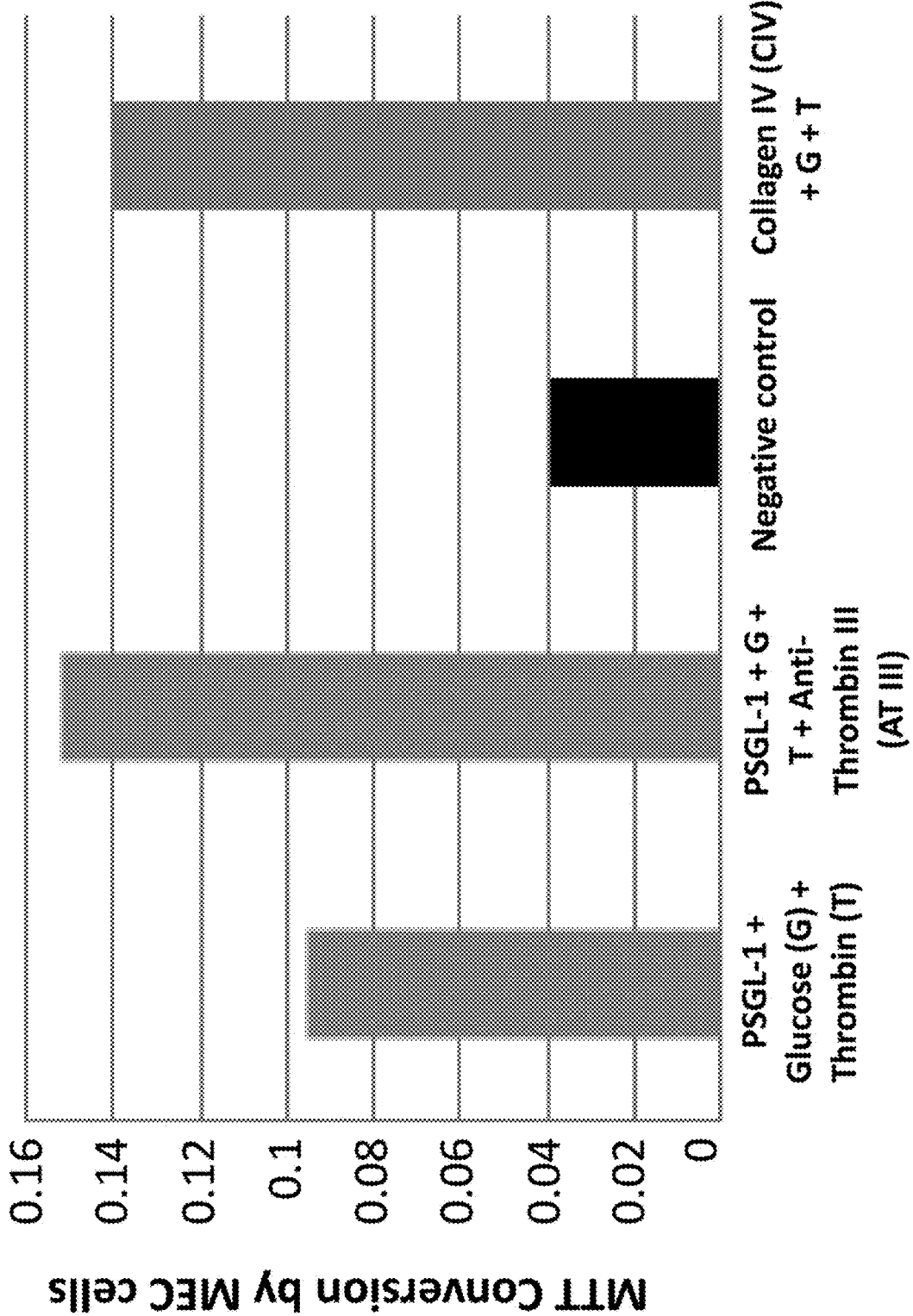
FIG. 9 shows the effect of pre-bound PSGIA and a solution-phase P-selectin inhibitor (anti-thrombin III; ATIII) (10 IU/mL) on the metabolic response of MEC to thrombin and glucose (10 mg/mL). Thrombin (T) and glucose (G) were added to the wells of a 24-well tissue culture plate prior to seeding of serum-starved MEC cells (50,000/well) and cultivated for 2 days and an MTT assay performed.

As shown in FIG. 9, anti-thrombin III (ATIII) stimulated the proliferation of MEC in the presence of thrombin (+glucose) and pre-bound PSGL-1.

The results of these experiments suggest that thrombin-induced P-selectin expression on the endothelial surface and/or matrix bound P-selectin inhibits endothelial proliferation and that the presence of P-selectin inhibitors, such as ATIII, aid endothelial proliferation by suppressing P-selectin expression.

The invention claimed is:

1. A method for treating a condition associated with aberrant keratinocyte epithelial cell proliferation, the method comprising:
   a) obtaining a sample of keratinocyte epithelial cells from a subject;
   b) determining the level of P-selectin expression in the sample;
   c) comparing the level of P-selectin expression to a reference value, wherein a level of P-selectin that is equal to or greater than the reference value is indicative of the presence of a condition associated with aberrant keratinocyte epithelial cell proliferation; and
   d) treating a subject identified in step c) as having a condition associated with aberrant keratinocyte epithelial cell proliferation with an effective amount of an agent that inhibits P-selectin expression and/or activity.

2. The method of claim 1, wherein step (b) comprises determining the level of P-selectin gene expression in the sample.

3. The method of claim 1, wherein step (b) comprises determining the level of P-selectin protein in the sample.

4. The method of claim 1, wherein the agent is selected from:
   i) an inhibitor of P-selectin gene expression selected from the group consisting of selected from the group consisting of mediators of RNA interference, ribozymes and CRISPR RNAs used in combination with Cas or other nucleases; and
   ii) an antagonist of P-selectin activity selected from the group consisting of selected from the group consisting of an anti-P-selectin antibody or antigen binding fragment thereof, ligand mimetics for P-selectin, P-selectin blockers and small molecule inhibitors of P-selectin activity.

5. The method of claim 4, wherein the agent is a siRNA.

6. The method of claim 4, wherein the agent is an anti-P-selectin antibody or an antigen-binding fragment thereof.

7. The method of claim 1, further comprising administering an effective amount of a second agent that inhibits Rho-kinase expression and/or activity to the subject.

8. The method of claim 1, wherein the condition associated with aberrant keratinocyte epithelial cell proliferation is cancer.

\* \* \* \* \*